United States Patent [19]

Appelbaum et al.

[11] Patent Number: 5,783,184
[45] Date of Patent: *Jul. 21, 1998

[54] METHOD FOR TREATMENT AND DIAGNOSIS OF IL-5 MEDIATED DISORDERS

[75] Inventors: Edward Robert Appelbaum, Blue Bell; Richard Murray Cook, Chester Springs, both of Pa.

[73] Assignee: SmithKline Beecham Corporation, Philadelphia, Pa.

[*] Notice: The term of this patent shall not extend beyond the expiration date of Pat. No. 5,693,323.

[21] Appl. No.: 667,769

[22] Filed: Jun. 21, 1996

Related U.S. Application Data

[63] Continuation-in-part of Ser. No. 470,110, PCT/US95/17082 filed Dec. 22, 1995, Pat. No. 5,693,323, and Ser. No. 467,420, Jun. 6, 1995, Pat. No. 5,683,892, which is a continuation-in-part of Ser. No. 363,131, Dec. 23, 1994, abandoned, said Ser. No. 470,110, is a continuation-in-part of Ser. No. 363,131.

[51] Int. Cl.$^6$ .................. A61K 39/395; A61K 39/40; G01N 33/53; C07K 16/00
[52] U.S. Cl. .................. 424/130.1; 424/133.1; 424/141.1; 424/145.1; 435/7.1; 530/388.1; 530/388.23
[58] Field of Search .................. 424/130.1, 133.1, 424/141.1, 145.1; 435/7.1; 530/388.1, 388.23

[56] References Cited

U.S. PATENT DOCUMENTS 4,980,359 12/1990 Hasspacker et al.
5,455,337 10/1995 Devos et al.

FOREIGN PATENT DOCUMENTS 367596 5/1990 European Pat. Off.

OTHER PUBLICATIONS

Morrison et al (PNAS USA vol. 81 Nov. 1984 pp. 6851–6855).

McNamee et al (J. of Immunological Methods vol. 141 (1991) pp. 81–88).

Dickason, et al., "Delineation of IL-5 Domains Predicted to Engage the IL-5 Receptor Complex", *J. Immunol.*, 156, pp. 1030–1037 (1996).

Dickason, et al., "Enhanced Detection of Human IL-5 In Biological Fluids Utilizing Murine Monoclonal Antibodies Which Delineate Distinct Neutralizing Epitopes", *Cytokine*, 6, pp. 647–656 (1994).

Cornelis, S., "Detailed analysis of the IL-5-IL-5Rα interaction: characterization of crucial residues on the ligand and the receptor", *The EMBO Journal*, 14 pp. 3395–3402 (1995).

Tavernier, J., "Identification of receptor-binding domains on human interleukin 5 and design of an interleukin 5-derived receptor antagonist", *Proc. Natl. Acad. Sci. USA*, 92, pp. 5194–5198 (1995).

Graber, P., "Identification of Key Charged Residues of Human Interleukin-5 in Receptor Binding and Cellular Activation", *The Journal of Biological Chemistry*, 270, pp. 15762–15769 (1995).

Migita, M., "Characterization of the human IL-5 receptors on eosinophils", *Cellular Immunology*, 133, pp. 484–497 (1991).

Rolink, A., "Monoclonal Antibodies Reactive With the Mouse Interleukin 5 Receptor", *J. Exp. Med.*, 169, 1693–1701 (1989).

Murata, Y., "Molecular Cloning and Expression of the Human Interleukin 5 Receptor", *J. Exp. Med.*, 175, pp. 341–351 (1992).

Tavernier, J., "Molecular basis of the membrane-anchored and two soluble isoforms of the human interleukin 5 receptor α subunit", *Proc. Natl. Sci. USA*, 89, pp. 7041–7045 (1992).

Abrams, J., Eosinophil-active aytokines in human disease: development and use of monoclonal antibodies to IL3, IL5, and GM-CSF Eosinophilis in Allergy and Inflammation, pp. 133–157 (1994).

Banks, M., "Soluble Iterleukin 5 Receptor α-Chain Binding Assays: Use for Screening and Analysis of Interleukin-5 Mutants", *Analytical Biochemistry*, 230, pp. 321–328 (1995).

Johanson, K., "Binding Interactions of Human Interleukin 5 with its Receptor α Subunit", *The Journal of Biological Chemistry*, 270, pp. 9459–9471 (1995).

*Primary Examiner*—Anthony C. Caputa
*Assistant Examiner*—Mark Navarro
*Attorney, Agent, or Firm*—Alissa M. Eagle; William T. King; Edward T. Lentz

[57] ABSTRACT

The present invention relates to treatment and diagnosis of conditions mediated by IL-5 and excess eosinophil production, and more specifically to mAbs and other altered antibodies such as Fabs, chimeric, human and humanized antibodies that do not block binding of human IL-5 to the α-chain of the human IL-5 receptor.

10 Claims, 13 Drawing Sheets

| | | | | | | | | | | |
|---|---|---|---|---|---|---|---|---|---|---|
| 1 | CCT Pro | GGC Gly | CTG Leu | GTG Val | GCG Ala | CCC Pro | TCA Ser | CAG Gln | AGC Ser | CTG Leu | 30 |
| 31 | TCC Ser | ATC Ile | ACT Thr | TGC Cys | ACT Thr | GTC Val | TCT Ser | GGG Gly | TTT Phe | TCA Ser | 60 |
| 61 | TTA Leu | ACC Thr | AGC Ser | TAT Tyr | AGT Ser | GTA Val | CAC His | TGG Trp | GTT Val | CGC Arg | 90 |
| 91 | CAG Gln | CCT Pro | CCA Pro | GGA Gly | AAG Lys | GGT Gly | CTG Leu | GAG Glu | TGG Trp | CTG Leu | 120 |
| 121 | GGA Gly | GTA Val | ATA Ile | TGG Trp | GCT Ala | AGT Ser | GGA Gly | GGC Gly | ACA Thr | GAT Asp | 150 |
| 151 | TAT Tyr | AAT Asn | TCG Ser | GCT Ala | CTC Leu | ATG Met | TCC Ser | AGA Arg | CTG Leu | AGC Ser | 180 |
| 181 | ATC Ile | AGC Ser | AAA Lys | GAC Asp | AAC Asn | TCC Ser | AAG Lys | AGC Ser | CAA Gln | GTT Val | 210 |
| 211 | TTC Phe | TTA Leu | AAA Lys | CTG Leu | AAC Asn | AGT Ser | CTG Leu | CAA Gln | ACT Thr | GAT Asp | 240 |
| 241 | GAC Asp | ACA Thr | GCC Ala | ATG Met | TAC Tyr | TAC Tyr | TGT Cys | GCC Ala | AGA Arg | GAT Asp | 270 |
| 271 | CCC Pro | CCT Pro | TCT Ser | TCC Ser | TTA Leu | CTA Leu | CGG Arg | CTT Leu | GAC Asp | TAC Tyr | 300 |
| 301 | TGG Trp | GGC Gly | CAA Gln | GGC Gly | ACC Thr | ACT Thr | CTC Leu | ACA Thr | GTC Val | TCC Ser | 330 |
| 331 | TCA Ser | | | | | | | | | | 333 |

FIG. 1

```
  1   TCC TCC CTG AGT GTG TCA GCA GGA GAG AAG    30
      Ser Ser Leu Ser Val Ser Ala Gly Glu Lys

31   GTC ACT ATG AGC TGC AAG TCC AGT CAG AGT    60
      Val Thr Met Ser Cys Lys Ser Ser Gln Ser

61   CTG TTA AAC AGT GGA AAT CAA AAG AAC TAC    90
      Leu Leu Asn Ser Gly Asn Gln Lys Asn Tyr

91   TTG GCC TGG TAC CAG CAG AAA CCA GGG CAG   120
      Leu Ala Trp Tyr Gln Gln Lys Pro Gly Gln

121   CCT CCT AAA CTT TTG ATC TAC GGG GCA TCC   150
      Pro Pro Lys Leu Leu Ile Tyr Gly Ala Ser

151   ACT AGG GAA TCT GGG GTC CCT GAT CGC TTC   180
      Thr Arg Glu Ser Gly Val Pro Asp Arg Phe

181   ACA GGC AGT GGA TCT GGA ACC GAT TTC ACT   210
      Thr Gly Ser Gly Ser Gly Thr Asp Phe Thr

211   CTT TCC ATC AGC AGT GTG CAG GCT GAA GAC   240
      Leu Ser Ile Ser Ser Val Gln Ala Glu Asp

241   CTG GCA GTT TAT TAC TGT CAG AAT GTT CAT   270
      Leu Ala Val Tyr Tyr Cys Gln Asn Val His

271   AGT TTT CCA TTC ACG TTC GGC TCG GGG ACA   300
      Ser Phe Pro Phe Thr Phe Gly Ser Gly Thr

301   GAG TTG GAA ATA AAA   315
      Glu Leu Glu Ile Lys
```

FIG. 2

| | | | | | | | | | | |
|---|---|---|---|---|---|---|---|---|---|---|
| 1 | CCT Pro | GGC Gly | CTG Leu | GTG Val | GCG Ala | CCC Pro | TCA Ser | CAG Gln | AGC Ser | CTG Leu | 30 |
| 31 | TCC Ser | ATC Ile | ACT Thr | TGC Cys | ACT Thr | GTC Val | TCT Ser | GGG Gly | TTT Phe | TCA Ser | 60 |
| 61 | TTA Leu | ACC Thr | AGT Ser | TAT Tyr | AGT Ser | GTA Val | CAC His | TGG Trp | GTT Val | CGC Arg | 90 |
| 91 | CAG Gln | CCT Pro | CCA Pro | GGA Gly | AAG Lys | GGT Gly | CTG Leu | GAG Glu | TGG Trp | CTG Leu | 120 |
| 121 | GGA Gly | GTA Val | ATA Ile | TGG Trp | GCT Ala | AGT Ser | GGA Gly | GGC Gly | ACA Thr | GAT Asp | 150 |
| 151 | TAT Tyr | AAT Asn | TCG Ser | GCT Ala | CTC Leu | ATG Met | TCC Ser | AGA Arg | CTG Leu | AGC Ser | 180 |
| 181 | ATC Ile | AGC Ser | AAA Lys | GAC Asp | AAC Asn | TCC Ser | AAG Lys | AGC Ser | CAA Gln | GTT Val | 210 |
| 211 | TTC Phe | TTA Leu | AAA Lys | CTG Leu | AAC Asn | AGT Ser | CTG Leu | CGA Arg | ACT Thr | GAT Asp | 240 |
| 241 | GAC Asp | ACA Thr | GCC Ala | ATG Met | TAC Tyr | TAC Tyr | TGT Cys | GCC Ala | AGA Arg | GAT Asp | 270 |
| 271 | CCC Pro | CCT Pro | TCT Ser | TCC Ser | TTA Leu | CTA Leu | CGG Arg | CTT Leu | GAC Asp | TAC Tyr | 300 |
| 301 | TGG Trp | GGC Gly | CAA Gln | GGC Gly | ACT Thr | ACT Thr | CTC Leu | ACA Thr | GTC Val | TCC Ser | 330 |
| 331 | TCA Ser | 333 | | | | | | | | | |

FIG. 3

| | | | | | | | | | | |
|---|---|---|---|---|---|---|---|---|---|---|
| 1 | TCC | TCC | CTG | AGT | GTG | TCA | GCA | GGA | GAG | AAG | 30 |
| | Ser | Ser | Leu | Ser | Val | Ser | Ala | Gly | Glu | Lys | |
| 31 | GTC | ACT | ATG | AGC | TGC | AAG | TCC | AGT | CAG | AGT | 60 |
| | Val | Thr | Met | Ser | Cys | Lys | Ser | Ser | Gln | Ser | |
| 61 | CTA | TTA | AAC | AGT | GGA | AAT | CAA | AAG | AAC | TAC | 90 |
| | Leu | Leu | Asn | Ser | Gly | Asn | Gln | Lys | Asn | Tyr | |
| 91 | TTG | GCC | TGG | TAC | CAA | CAG | AAA | CCA | GGG | CAG | 120 |
| | Leu | Ala | Trp | Tyr | Gln | Gln | Lys | Pro | Gly | Gln | |
| 121 | CCT | CCT | AAA | CTT | TTG | ATC | TAC | GGG | GCA | TCC | 150 |
| | Pro | Pro | Lys | Leu | Leu | Ile | Tyr | Gly | Ala | Ser | |
| 151 | ACT | AGG | GAA | TCT | GGG | GTC | CCT | GAT | CGC | TTC | 180 |
| | Thr | Arg | Glu | Ser | Gly | Val | Pro | Asp | Arg | Phe | |
| 181 | ACA | GGC | AGT | GGA | TCT | GGA | ACC | GAT | TTC | ACT | 210 |
| | Thr | Gly | Ser | Gly | Ser | Gly | Thr | Asp | Phe | Thr | |
| 211 | CTT | ACC | ATC | AGC | AGT | GTG | CAG | GCT | GAA | GAC | 240 |
| | Leu | Thr | Ile | Ser | Ser | Val | Gln | Ala | Glu | Asp | |
| 241 | CTG | GCA | GTT | TAT | TAC | TGT | CAG | AAT | GAT | CAT | 270 |
| | Leu | Ala | Val | Tyr | Tyr | Cys | Gln | Asn | Asp | His | |
| 271 | AGT | TTT | CCA | TTC | ACG | TTC | GGC | TCG | GGG | ACA | 300 |
| | Ser | Phe | Pro | Phe | Thr | Phe | Gly | Ser | Gly | Thr | |
| 301 | GAG | TTG | GAA | ATA | AAA | 315 | | | | | |
| | Glu | Leu | Glu | Ile | Lys | | | | | | |

FIG. 4

| | | | | | | | | | | |
|---|---|---|---|---|---|---|---|---|---|---|
| 1 | CCT Pro | GGC Gly | CTG Leu | GTG Val | GCG Ala | CCC Pro | TCA Ser | CAG Gln | AGC Ser | CTG Leu | 30 |
| 31 | TCC Ser | ATC Ile | ACT Thr | TGC Cys | ACT Thr | GTC Val | TCT Ser | GGG Gly | TTT Phe | TCA Ser | 60 |
| 61 | TTA Leu | ACC Thr | AGC Ser | TAT Tyr | AGT Ser | GTA Val | CAC His | TGG Trp | GTT Val | CGC Arg | 90 |
| 91 | CAG Gln | CCT Pro | CCA Pro | GGA Gly | AAG Lys | GGT Gly | CTG Leu | GAG Glu | TGG Trp | CTG Leu | 120 |
| 121 | GGA Gly | GTA Val | ATC Ile | TGG Trp | GCT Ala | AGT Ser | GGA Gly | GGC Gly | ACA Thr | GAT Asp | 150 |
| 151 | TAT Tyr | AAT Asn | TCG Ser | GCT Ala | CTC Leu | ATG Met | TCC Ser | AGA Arg | CTG Leu | AGC Ser | 180 |
| 181 | ATC Ile | AGC Ser | AAA Lys | GAC Asp | AAC Asn | TCC Ser | AAG Lys | AGC Ser | CAA Gln | GTT Val | 210 |
| 211 | TTC Phe | TTA Leu | AAA Lys | CTG Leu | AAC Asn | AGT Ser | CTG Leu | CAA Gln | ACT Thr | GAT Asp | 240 |
| 241 | GAC Asp | GCA Ala | GCC Ala | ATG Met | TAC Tyr | TAC Tyr | TGT Cys | GCC Ala | AGA Arg | GAT Asp | 270 |
| 271 | CCC Pro | CCT Pro | TTT Phe | TCC Ser | TTA Leu | CTA Leu | CGG Arg | CTT Leu | GAC Asp | TTC Phe | 300 |
| 301 | TGG Trp | GGC Gly | CAA Gln | GGC Gly | ACC Thr | ACT Thr | CTC Leu | ACA Thr | GTC Val | TCC Ser | 330 |
| 331 | TCA Ser | 333 | | | | | | | | | |

FIG. 5

| | | | | | | | | | | |
|---|---|---|---|---|---|---|---|---|---|---|
| 1 | TCC | TCT | CTG | AGT | GTG | TCA | GCA | GGA | GAG | AAG | 30 |
| | Ser | Ser | Leu | Ser | Val | Ser | Ala | Gly | Glu | Lys | |
| 31 | GTC | ACT | ATG | AGC | TGC | AAG | TCC | AGT | CAG | AGT | 60 |
| | Val | Thr | Met | Ser | Cys | Lys | Ser | Ser | Gln | Ser | |
| 61 | CTG | TTA | AAC | AGT | GGA | AAT | CAA | AAA | AAC | TAC | 90 |
| | Leu | Leu | Asn | Ser | Gly | Asn | Gln | Lys | Asn | Tyr | |
| 91 | TTG | GCC | TGG | TAC | CAG | CAG | AAA | CCA | GGG | CAG | 120 |
| | Leu | Ala | Trp | Tyr | Gln | Gln | Lys | Pro | Gly | Gln | |
| 121 | CCT | CCT | AAA | CTT | TTG | ATC | TAC | GGG | GCA | TCC | 150 |
| | Pro | Pro | Lys | Leu | Leu | Ile | Tyr | Gly | Ala | Ser | |
| 151 | ACT | AGG | GAA | TCT | GGG | GTC | CCT | GAT | CGC | TTC | 180 |
| | Thr | Arg | Glu | Ser | Gly | Val | Pro | Asp | Arg | Phe | |
| 181 | ACA | GGC | AGT | GGA | TCT | GGA | ACC | GAT | TTC | ACT | 210 |
| | Thr | Gly | Ser | Gly | Ser | Gly | Thr | Asp | Phe | Thr | |
| 211 | CTT | ACC | ATC | AGC | AGT | GTG | CAG | GCT | GAA | GAC | 240 |
| | Leu | Thr | Ile | Ser | Ser | Val | Gln | Ala | Glu | Asp | |
| 241 | CTG | GCA | GTT | TAT | TAC | TGT | CAG | AAT | GAT | CAT | 270 |
| | Leu | Ala | Val | Tyr | Tyr | Cys | Gln | Asn | Asp | His | |
| 271 | AGT | TTT | CCA | TTC | ACG | TTC | GGC | TCG | GGG | ACA | 300 |
| | Ser | Phe | Pro | Phe | Thr | Phe | Gly | Ser | Gly | Thr | |
| 301 | GAG | TTG | GAA | ATA | AAA | 315 | | | | | |
| | Glu | Leu | Glu | Ile | Lys | | | | | | |

FIG. 6

2B6 CDRs

HEAVY CHAIN 1: SYSVH
HEAVY CHAIN 2: VIWASGGTDYNSALMS
HEAVY CHAIN 3: DPPSSLLRLDY

LIGHT CHAIN 1: KSSQSLLNSGNQKNYLA
LIGHT CHAIN 2: GASTRES
LIGHT CHAIN 3: QNVHSFPFT

2F2 CDRs

HEAVY CHAIN 1: SYSVH
HEAVY CHAIN 2: VIWASGGTDYNSALMS
HEAVY CHAIN 3: DPPSSLLRLDY

LIGHT CHAIN 1: KSSQSLLNSGNQKNYLA
LIGHT CHAIN 2: GASTRES
LIGHT CHAIN 3: QNDHSFPFT

2E3 CDRs

HEAVY CHAIN 1: SYSVH
HEAVY CHAIN 2: VIWASGGTDYNSALMS
HEAVY CHAIN 3: DPPFSLLRLDF

LIGHT CHAIN 1: KSSQSLLNSGNQKNYLA
LIGHT CHAIN 2: GASTRES
LIGHT CHAIN 3: QNDHSFPFT

FIG. 7

| | | | | | | | | | | |
|---|---|---|---|---|---|---|---|---|---|---|
| 1 | CAG | GTT | ACC | CTG | CGT | GAA | TCC | GGT | CCG | GCA | 30 |
| | Gln | Val | Thr | Leu | Arg | Glu | Ser | Gly | Pro | Ala | |
| 31 | CTA | GTT | AAA | CCG | ACC | CAG | ACC | CTG | ACG | TTA | 60 |
| | Leu | Val | Lys | Pro | Thr | Gln | Thr | Leu | Thr | Leu | |
| 61 | ACC | TGC | ACC | GTC | TCC | GGT | TTC | TCC | CTG | ACG | 90 |
| | Thr | Cys | Thr | Val | Ser | Gly | Phe | Ser | Leu | Thr | |
| 91 | AGC | TAT | AGT | GTA | CAC | TGG | GTC | CGT | CAG | CCG | 120 |
| | Ser | Tyr | Ser | Val | His | Trp | Val | Arg | Gln | Pro | |
| 121 | CCG | GGT | AAA | GGT | CTA | GAA | TGG | CTG | GGT | GTA | 150 |
| | Pro | Gly | Lys | Gly | Leu | Glu | Trp | Leu | Gly | Val | |
| 151 | ATA | TGG | GCT | AGT | GGA | GGC | ACA | GAT | TAT | AAT | 180 |
| | Ile | Trp | Ala | Ser | Gly | Gly | Thr | Asp | Tyr | Asn | |
| 181 | TCG | GCT | CTC | ATG | TCC | CGT | CTG | TCG | ATA | TCC | 210 |
| | Ser | Ala | Leu | Met | Ser | Arg | Leu | Ser | Ile | Ser | |
| 211 | AAA | GAC | ACC | TCC | CGT | AAC | CAG | GTT | GTT | CTG | 240 |
| | Lys | Asp | Thr | Ser | Arg | Asn | Gln | Val | Val | Leu | |
| 241 | ACC | ATG | ACT | AAC | ATG | GAC | CCG | GTT | GAC | ACC | 270 |
| | Thr | Met | Thr | Asn | Met | Asp | Pro | Val | Asp | Thr | |
| 271 | GCT | ACC | TAC | TAC | TGC | GCT | CGA | GAT | CCC | CCT | 300 |
| | Ala | Thr | Tyr | Tyr | Cys | Ala | Arg | Asp | Pro | Pro | |
| 301 | TCT | TCC | TTA | CTA | CGG | CTT | GAC | TAC | TGG | GGT | 330 |
| | Ser | Ser | Leu | Leu | Arg | Leu | Asp | Tyr | Trp | Gly | |
| 331 | CGT | GGT | ACC | CCA | GTT | ACC | GTG | AGC | TCA | | 357 |
| | Arg | Gly | Thr | Pro | Val | Thr | Val | Ser | Ser | | |

FIG. 8

| | | | | | | | | | | |
|---|---|---|---|---|---|---|---|---|---|---|
| 1 | GAT | ATC | GTG | ATG | ACC | CAG | TCT | CCA | GAC | TCG | 30 |
| | Asp | Ile | Val | Met | Thr | Gln | Ser | Pro | Asp | Ser | |
| 31 | CTA | GCT | GTG | TCT | CTG | GGC | GAG | AGG | GCC | ACC | 60 |
| | Leu | Ala | Val | Ser | Leu | Gly | Glu | Arg | Ala | Thr | |
| 61 | ATC | AAC | TGC | AAG | AGC | TCT | CAG | AGT | CTG | TTA | 90 |
| | Ile | Asn | Cys | Lys | Ser | Ser | Gln | Ser | Leu | Leu | |
| 91 | AAC | AGT | GGA | AAT | CAA | AAG | AAC | TAC | TTG | GCC | 120 |
| | Asn | Ser | Gly | Asn | Gln | Lys | Asn | Tyr | Leu | Ala | |
| 121 | TGG | TAT | CAG | CAG | AAA | CCC | GGG | CAG | CCT | CCT | 150 |
| | Trp | Tyr | Gln | Gln | Lys | Pro | Gly | Gln | Pro | Pro | |
| 151 | AAG | TTG | CTC | ATT | TAC | GGG | GCG | TCG | ACT | AGG | 180 |
| | Lys | Leu | Leu | Ile | Tyr | Gly | Ala | Ser | Thr | Arg | |
| 181 | GAA | TCT | GGG | GTA | CCT | GAC | CGA | TTC | AGT | GGC | 210 |
| | Glu | Ser | Gly | Val | Pro | Asp | Arg | Phe | Ser | Gly | |
| 211 | AGC | GGG | TCT | GGG | ACA | GAT | TTC | ACT | CTC | ACC | 240 |
| | Ser | Gly | Ser | Gly | Thr | Asp | Phe | Thr | Leu | Thr | |
| 241 | ATC | AGC | AGC | CTG | CAG | GCT | GAA | GAT | GTG | GCA | 270 |
| | Ile | Ser | Ser | Leu | Gln | Ala | Glu | Asp | Val | Ala | |
| 271 | GTA | TAC | TAC | TGT | CAG | AAT | GTT | CAT | AGT | TTT | 300 |
| | Val | Tyr | Tyr | Cys | Gln | Asn | Val | His | Ser | Phe | |
| 301 | CCA | TTC | ACG | TTC | GGC | GGA | GGG | ACC | AAG | TTG | 330 |
| | Pro | Phe | Thr | Phe | Gly | Gly | Gly | Thr | Lys | Leu | |
| 331 | GAG | ATC | AAA | | | | | | | | 339 |
| | Glu | Ile | Lys | | | | | | | | |

FIG. 9

| | | | | | | | | | | |
|---|---|---|---|---|---|---|---|---|---|---|
| 1 | CAG | GTC | CAA | CTG | CAG | GAG | AGC | GGT | CCA | GGT | 30 |
| | Gln | Val | Gln | Leu | Gln | Glu | Ser | Gly | Pro | Gly | |
| 31 | CTT | GTG | AGA | CCT | AGC | CAG | ACC | CTG | AGC | CTG | 60 |
| | Leu | Val | Arg | Pro | Ser | Gln | Thr | Leu | Ser | Leu | |
| 61 | ACC | TGC | ACC | GTC | TCG | GGC | TTC | TCC | CTC | ACC | 90 |
| | Thr | Cys | Thr | Val | Ser | Gly | Phe | Ser | Leu | Thr | |
| 91 | AGC | TAT | AGT | GTA | CAC | TGG | GTG | AGA | CAG | CCA | 120 |
| | Ser | Tyr | Ser | Val | His | Trp | Val | Arg | Gln | Pro | |
| 121 | CCT | GGA | CGA | GGT | CTA | GAG | TGG | CTT | GGA | GTA | 150 |
| | Pro | Gly | Arg | Gly | Leu | Glu | Trp | Leu | Gly | Val | |
| 151 | ATA | TGG | GCT | AGT | GGA | GGC | ACA | GAT | TAT | AAT | 180 |
| | Ile | Trp | Ala | Ser | Gly | Gly | Thr | Asp | Tyr | Asn | |
| 181 | TCG | GCT | CTC | ATG | TCC | AGA | CTG | TCA | ATA | CTG | 210 |
| | Ser | Ala | Leu | Met | Ser | Arg | Leu | Ser | Ile | Leu | |
| 211 | AAA | GAC | AAC | AGC | AAG | AAC | CAG | GTC | AGC | CTG | 240 |
| | Lys | Asp | Asn | Ser | Lys | Asn | Gln | Val | Ser | Leu | |
| 241 | AGA | CTC | AGC | AGC | GTG | ACA | GCC | GCC | GAC | ACC | 270 |
| | Arg | Leu | Ser | Ser | Val | Thr | Ala | Ala | Asp | Thr | |
| 271 | GCG | GTC | TAT | TTC | TGT | GCT | CGA | GAT | CCC | CCT | 300 |
| | Ala | Val | Tyr | Phe | Cys | Ala | Arg | Asp | Pro | Pro | |
| 301 | TCT | TCC | TTA | CTA | CGG | CTT | GAC | TAC | TGG | GGA | 330 |
| | Ser | Ser | Leu | Leu | Arg | Leu | Asp | Tyr | Trp | Gly | |
| 331 | CAA | GGT | ACC | ACG | GTC | ACC | GTC | TCG | AGC | | 357 |
| | Gln | Gly | Thr | Thr | Val | Thr | Val | Ser | Ser | | |

FIG. 12

| | | | | | | | | | | |
|---|---|---|---|---|---|---|---|---|---|---|
| 1 | GAT | ATC | GTG | ATG | ACC | CAG | AGC | CCA | AGC | AGC | 30 |
| | Asp | Ile | Val | Met | Thr | Gln | Ser | Pro | Ser | Ser | |
| 31 | CTG | AGC | GCT | AGC | GTG | GGT | GAC | AGA | GTG | ACC | 60 |
| | Leu | Ser | Ala | Ser | Val | Gly | Asp | Arg | Val | Thr | |
| 61 | ATC | ACC | TGT | AAG | AGC | TCT | CAG | AGT | CTG | TTA | 90 |
| | Ile | Thr | Cys | Lys | Ser | Ser | Gln | Ser | Leu | Leu | |
| 91 | AAC | AGT | GGA | AAT | CAA | AAG | AAC | TAC | TTG | GCC | 120 |
| | Asn | Ser | Gly | Asn | Gln | Lys | Asn | Tyr | Leu | Ala | |
| 121 | TGG | TAT | CAG | CAG | AAA | CCC | GGT | AAG | GCT | CCA | 150 |
| | Trp | Tyr | Gln | Gln | Lys | Pro | Gly | Lys | Ala | Pro | |
| 151 | AAG | CTG | CTG | ATC | TAC | GGG | GCA | TCG | ACT | AGG | 180 |
| | Lys | Leu | Leu | Ile | Tyr | Gly | Ala | Ser | Thr | Arg | |
| 181 | GAA | TCT | GGG | GTA | CCA | GAT | AGA | TTC | AGC | GGT | 210 |
| | Glu | Ser | Gly | Val | Pro | Asp | Arg | Phe | Ser | Gly | |
| 211 | AGC | GGT | AGC | GGA | ACC | GAC | TTC | ACC | TTC | ACC | 240 |
| | Ser | Gly | Ser | Gly | Thr | Asp | Phe | Thr | Phe | Thr | |
| 241 | ATC | AGC | AGC | CTG | CAG | CCA | GAG | GAC | ATC | GCC | 270 |
| | Ile | Ser | Ser | Leu | Gln | Pro | Glu | Asp | Ile | Ala | |
| 271 | ACC | TAC | TAC | TGC | CAG | AAT | GTT | CAT | AGT | TTT | 300 |
| | Thr | Tyr | Tyr | Cys | Gln | Asn | Val | His | Ser | Phe | |
| 301 | CCA | TTC | ACG | TTC | GGA | CAA | GGG | ACC | AAG | GTG | 330 |
| | Pro | Phe | Thr | Phe | Gly | Gln | Gly | Thr | Lys | Val | |
| 331 | GAG | ATC | AAA | 339 | | | | | | | |
| | Glu | Ile | Lys | | | | | | | | |

FIG. 13

SEQUENCE LISTING ( 1 ) GENERAL INFORMATION:

( i i i ) NUMBER OF SEQUENCES: 76

( 2 ) INFORMATION FOR SEQ ID NO:1:

( i ) SEQUENCE CHARACTERISTICS:
        ( A ) LENGTH: 334 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..334
        ( D ) OTHER INFORMATION: /note= "First base corresponds to
            Kabat position 24"

( x i ) SEQUENCE DESCRIPTION: SEQ ID NO:1:

```
ACCTGGCCTG GTGGCGCCCT CACAGAGCCT GTCCATCACT TGCACTGTCT CTGGGTTTTC      60
ATTAACCAGC TATAGTGTAC ACTGGGTTCG CCAGCCTCCA GGAAAGGGTC TGGAGTGGCT     120
GGGAGTAATA TGGGCTAGTG GAGGCACAGA TTATAATTCG GCTCTCATGT CCAGACTGAG     180
CATCAGCAAA GACAACTCCA AGAGCCAAGT TTTCTTAAAA CTGAACAGTC TGCAAACTGA     240
TGACACAGCC ATGTACTACT GTGCCAGAGA TCCCCCTTCT TCCTTACTAC GGCTTGACTA     300
CTGGGGCCAA GGCACCACTC TCACAGTCTC CTCA                                 334
```

( 2 ) INFORMATION FOR SEQ ID NO:2:

( i ) SEQUENCE CHARACTERISTICS:
        ( A ) LENGTH: 315 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..315
        ( D ) OTHER INFORMATION: /note= "First base corresponds to
            Kabat position 25"

( x i ) SEQUENCE DESCRIPTION: SEQ ID NO:2:

```
TCCTCCCTGA GTGTGTCAGC AGGAGAGAAG GTCACTATGA GCTGCAAGTC CAGTCAGAGT      60
CTGTTAAACA GTGGAAATCA AAAGAACTAC TTGGCCTGGT ACCAGCAGAA ACCAGGGCAG     120
CCTCCTAAAC TTTTGATCTA CGGGGCATCC ACTAGGGAAT CTGGGGTCCC TGATCGCTTC     180
ACAGGCAGTG GATCTGGAAC CGATTTCACT CTTTCCATCA GCAGTGTGCA GGCTGAAGAC     240
CTGGCAGTTT ATTACTGTCA GAATGTTCAT AGTTTTCCAT TCACGTTCGG CTCGGGGACA     300
GAGTTGGAAA TAAAA                                                      315
```

( 2 ) INFORMATION FOR SEQ ID NO:3:

( i ) SEQUENCE CHARACTERISTICS:
        ( A ) LENGTH: 334 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( A ) NAME/KEY: misc_feature
    ( B ) LOCATION: 1..334
    ( D ) OTHER INFORMATION: /note= "First base corresponds to Kabat position 24"

( x i ) SEQUENCE DESCRIPTION: SEQ ID NO:3:

| | | | | | |
|---|---|---|---|---|---|
| ACCTGGCCTG | GTGGCGCCCT | CACAGAGCCT | GTCCATCACT | TGCACTGTCT | CTGGGTTTTC | 60 |
| ATTAACCAGT | TATAGTGTAC | ACTGGGTTCG | CCAGCCTCCA | GGAAAGGGTC | TGGAGTGGCT | 120 |
| GGGAGTAATA | TGGGCTAGTG | GAGGCACAGA | TTATAATTCG | GCTCTCATGT | CCAGACTGAG | 180 |
| CATCAGCAAA | GACAACTCCA | AGAGCCAAGT | TTTCTTAAAA | CTGAACAGTC | TGCGAACTGA | 240 |
| TGACACAGCC | ATGTACTACT | GTGCCAGAGA | TCCCCCTTCT | TCCTTACTAC | GGCTTGACTA | 300 |
| CTGGGGCCAA | GGCACCACTC | TCACAGTCTC | CTCA | | | 334 |

( 2 ) INFORMATION FOR SEQ ID NO:4:

( i ) SEQUENCE CHARACTERISTICS:
    ( A ) LENGTH: 315 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..315
    ( D ) OTHER INFORMATION: /note= "First base corresponds to Kabat 25"

( x i ) SEQUENCE DESCRIPTION: SEQ ID NO:4:

| | | | | | |
|---|---|---|---|---|---|
| TCCTCCCTGA | GTGTGTCAGC | AGGAGAGAAG | GTCACTATGA | GCTGCAAGTC | CAGTCAGAGT | 60 |
| CTATTAAACA | GTGGAAATCA | AAAGAACTAC | TTGGCCTGGT | ACCAACAGAA | ACCAGGGCAG | 120 |
| CCTCCTAAAC | TTTTGATCTA | CGGGGCATCC | ACTAGGGAAT | CTGGGGTCCC | TGATCGCTTC | 180 |
| ACAGGCAGTG | GATCTGGAAC | CGATTTCACT | CTTACCATCA | GCAGTGTGCA | GGCTGAAGAC | 240 |
| CTGGCAGTTT | ATTACTGTCA | GAATGATCAT | AGTTTTCCAT | TCACGTTCGG | CTCGGGGACA | 300 |
| GAGTTGGAAA | TAAAA | | | | | 315 |

( 2 ) INFORMATION FOR SEQ ID NO:5:

( i ) SEQUENCE CHARACTERISTICS:
    ( A ) LENGTH: 334 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..334
    ( D ) OTHER INFORMATION: /note= "First base corresponds to Kabat position 24"

( x i ) SEQUENCE DESCRIPTION: SEQ ID NO:5:

| | | | | | |
|---|---|---|---|---|---|
| ACCTGGCCTG | GTGGCGCCCT | CACAGAGCCT | GTCCATCACT | TGCACTGTCT | CTGGGTTTTC | 60 |
| ATTAACCAGC | TATAGTGTAC | ACTGGGTTCG | CCAGCCTCCA | GGAAAGGGTC | TGGAGTGGCT | 120 |
| GGGAGTAATC | TGGGCTAGTG | GAGGCACAGA | TTATAATTCG | GCTCTCATGT | CCAGACTGAG | 180 |
| CATCAGCAAA | GACAACTCCA | AGAGCCAAGT | TTTCTTAAAA | CTGAACAGTC | TGCAAACTGA | 240 |
| TGACGCAGCC | ATGTACTACT | GTGCCAGAGA | TCCCCCTTTT | TCCTTACTAC | GGCTTGACTT | 300 |

```
CTGGGGCCAA GGCACCACTC TCACAGTCTC CTCA                                              334
```

( 2 ) INFORMATION FOR SEQ ID NO:6:

( i ) SEQUENCE CHARACTERISTICS:
        ( A ) LENGTH: 315 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..315
        ( D ) OTHER INFORMATION: /note= "First base corresponds to
            Kabat position 25"

( x i ) SEQUENCE DESCRIPTION: SEQ ID NO:6:

```
TCCTCTCTGA GTGTGTCAGC AGGAGAGAAG GTCACTATGA GCTGCAAGTC CAGTCAGAGT     60

CTGTTAAACA GTGGAAATCA AAAAACTAC  TTGGCCTGGT ACCAGCAGAA ACCAGGGCAG    120

CCTCCTAAAC TTTTGATCTA CGGGGCATCC ACTAGGGAAT CTGGGGTCCC TGATCGCTTC    180

ACAGGCAGTG GATCTGGAAC CGATTTCACT CTTACCATCA GCAGTGTGCA GGCTGAAGAC    240

CTGGCAGTTT ATTACTGTCA GAATGATCAT AGTTTTCCAT TCACGTTCGG CTCGGGACA    300

GAGTTGGAAA TAAAA                                                    315
```

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Ser Tyr Ser Val His
1           5
```

( 2 ) INFORMATION FOR SEQ ID NO:8:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Val Ile Trp Ala Ser Gly Gly Thr Asp Tyr Asn Ser Ala Leu Met Ser
1               5                   10                  15
```

( 2 ) INFORMATION FOR SEQ ID NO:9:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

```
Asp Pro Pro Ser Ser Leu Leu Arg Leu Asp Tyr
1               5                   10
```

(2) INFORMATION FOR SEQ ID NO:10:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Lys Ser Ser Gln Ser Leu Leu Asn Ser Gly Asn Gln Lys Asn Tyr Leu
1               5                   10                  15
Ala
```

(2) INFORMATION FOR SEQ ID NO:11:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

```
Gly Ala Ser Thr Arg Glu Ser
1               5
```

(2) INFORMATION FOR SEQ ID NO:12:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Gln Asn Val His Ser Phe Pro Phe Thr
1               5
```

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

```
Gln Asn Asp His Ser Phe Pro Phe Thr
1               5
```

(2) INFORMATION FOR SEQ ID NO:14:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

Asp Pro Pro Phe Ser Leu Leu Arg Leu Asp Phe
1               5                   10

( 2 ) INFORMATION FOR SEQ ID NO:15:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:15:

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
                20                  25                  30

Ser Val His Trp Val Arg Gln Pro Gly Lys Gly Leu Glu Trp Leu
            35                  40                  45

Gly Val Ile Trp Ala Ser Gly Gly Thr Asp Tyr Asn Ser Ala Leu Met
        50                  55                  60

Ser Arg Leu Ser Ile Ser Lys Asp Asn Ser Lys Ser Gln Val Phe Leu
65                      70                  75                  80

Lys Leu Asn Ser Leu Gln Thr Asp Asp Thr Ala Met Tyr Tyr Cys Ala
                85                  90                  95

Arg Asp Pro Pro Ser Ser Leu Leu Arg Leu Asp Tyr Trp Gly Gln Gly
            100                 105                 110

Thr Thr Leu Thr Val Ser Ser
            115

( 2 ) INFORMATION FOR SEQ ID NO:16:

( i ) SEQUENCE CHARACTERISTICS:
        ( A ) LENGTH: 113 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:16:

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Ala Trp Tyr Gln Gln Lys Pro Gly Gln
            35                  40                  45

Pro Pro Lys Leu Leu Ile Tyr Gly Ala Ser Thr Arg Glu Ser Gly Val
        50                  55                  60

Pro Asp Arg Phe Thr Gly Ser Gly Ser Gly Thr Asp Phe Thr Leu Ser
65                      70                  75                  80

Ile Ser Ser Val Gln Ala Glu Asp Leu Ala Val Tyr Tyr Cys Gln Asn
                85                  90                  95

Val His Ser Phe Pro Phe Thr Phe Gly Ser Gly Thr Glu Leu Glu Ile
            100                 105                 110

Lys ( 2 ) INFORMATION FOR SEQ ID NO:17:

( i ) SEQUENCE CHARACTERISTICS:

( A ) LENGTH: 60 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

| ATGGTGTTGC | AGACCCAGGT | CTTCATTTCT | CTGTTGCTCT | GGATCTCTGG | TGCCTACGGG | 60 |

( 2 ) INFORMATION FOR SEQ ID NO:18:

( i ) SEQUENCE CHARACTERISTICS:
( A ) LENGTH: 357 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

| CAGGTTACCC | TGCGTGAATC | CGGTCCGGCA | CTAGTTAAAC | CGACCCAGAC | CCTGACGTTA | 60 |
| ACCTGCACCG | TCTCCGGTTT | CTCCCTGACG | AGCTATAGTG | TACACTGGGT | CCGTCAGCCG | 120 |
| CCGGGTAAAG | GTCTAGAATG | GCTGGGTGTA | ATATGGGCTA | GTGGAGGCAC | AGATTATAAT | 180 |
| TCGGCTCTCA | TGTCCCGTCT | GTCGATATCC | AAAGACACCT | CCCGTAACCA | GGTTGTTCTG | 240 |
| ACCATGACTA | ACATGGACCC | GGTTGACACC | GCTACCTACT | ACTGCGCTCG | AGATCCCCCT | 300 |
| TCTTCCTTAC | TACGGCTTGA | CTACTGGGGT | CGTGGTACCC | CAGTTACCGT | GAGCTCA | 357 |

( 2 ) INFORMATION FOR SEQ ID NO:19:

( i ) SEQUENCE CHARACTERISTICS:
( A ) LENGTH: 119 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:19:

| Gln | Val | Thr | Leu | Arg | Glu | Ser | Gly | Pro | Ala | Leu | Val | Lys | Pro | Thr | Gln |
| 1 | | | | 5 | | | | | 10 | | | | | 15 | |

| Thr | Leu | Thr | Leu | Thr | Cys | Thr | Val | Ser | Gly | Phe | Ser | Leu | Thr | Ser | Tyr |
| | | | 20 | | | | | 25 | | | | | 30 | | |

| Ser | Val | His | Trp | Val | Arg | Gln | Pro | Pro | Gly | Lys | Gly | Leu | Glu | Trp | Leu |
| | | | 35 | | | | | 40 | | | | | 45 | | |

| Gly | Val | Ile | Trp | Ala | Ser | Gly | Gly | Thr | Asp | Tyr | Asn | Ser | Ala | Leu | Met |
| | | | 50 | | | | | 55 | | | | | 60 | | |

| Ser | Arg | Leu | Ser | Ile | Ser | Lys | Asp | Thr | Ser | Arg | Asn | Gln | Val | Val | Leu |
| 65 | | | | | 70 | | | | | 75 | | | | | 80 |

| Thr | Met | Thr | Asn | Met | Asp | Pro | Val | Asp | Thr | Ala | Thr | Tyr | Tyr | Cys | Ala |
| | | | | 85 | | | | | 90 | | | | | 95 | |

| Arg | Asp | Pro | Pro | Ser | Ser | Leu | Leu | Arg | Leu | Asp | Tyr | Trp | Gly | Arg | Gly |
| | | | 100 | | | | | 105 | | | | | 110 | | |

| Thr | Pro | Val | Thr | Val | Ser | Ser |
| | | | 115 | | | |

( 2 ) INFORMATION FOR SEQ ID NO:20:

( i ) SEQUENCE CHARACTERISTICS:
( A ) LENGTH: 339 base pairs
( B ) TYPE: nucleic acid
( C ) STRANDEDNESS: single ( D ) TOPOLOGY: linear ( i i ) MOLECULE TYPE: DNA (genomic)

( x i ) SEQUENCE DESCRIPTION: SEQ ID NO:20:

| | | | | | |
|---|---|---|---|---|---|
| GATATCGTGA | TGACCCAGTC | TCCAGACTCG | CTAGCTGTGT | CTCTGGGCGA | GAGGGCCACC | 60 |
| ATCAACTGCA | AGAGCTCTCA | GAGTCTGTTA | AACAGTGGAA | ATCAAAAGAA | CTACTTGGCC | 120 |
| TGGTATCAGC | AGAAACCCGG | GCAGCCTCCT | AAGTTGCTCA | TTTACGGGGC | GTCGACTAGG | 180 |
| GAATCTGGGG | TACCTGACCG | ATTCAGTGGC | AGCGGGTCTG | GGACAGATTT | CACTCTCACC | 240 |
| ATCAGCAGCC | TGCAGGCTGA | AGATGTGGCA | GTATACTACT | GTCAGAATGT | TCATAGTTTT | 300 |
| CCATTCACGT | TCGGCGGAGG | GACCAAGTTG | GAGATCAAA | | | 339 |

( 2 ) INFORMATION FOR SEQ ID NO:21:

( i ) SEQUENCE CHARACTERISTICS:
       ( A ) LENGTH: 113 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO:21:

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
             20                  25                  30

Gly Asn Gln Lys Asn Tyr Leu Ala Trp Tyr Gln Gln Lys Pro Gly Gln
         35                  40                  45

Pro Pro Lys Leu Leu Ile Tyr Gly Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95

Val His Ser Phe Pro Phe Thr Phe Gly Gly Gly Thr Lys Leu Glu Ile
             100                 105                 110

Lys
```

( 2 ) INFORMATION FOR SEQ ID NO:22:

( i ) SEQUENCE CHARACTERISTICS:
       ( A ) LENGTH: 29 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:22:

GTACATATGC AAGGCTTACA ACCACAATC                                        29

( 2 ) INFORMATION FOR SEQ ID NO:23:

( i ) SEQUENCE CHARACTERISTICS:
       ( A ) LENGTH: 32 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:23:

GGACAGGGCT TACTAGTGGG CCCTCTGGGC TC 32

( 2 ) INFORMATION FOR SEQ ID NO:24:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

AGGTSMARCT KTCTCGAGTC WGG 23

( 2 ) INFORMATION FOR SEQ ID NO:25:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

CTAACACTCA TTCCTGTTGA AGCTCTTGAC AATGGG 36

( 2 ) INFORMATION FOR SEQ ID NO:26:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

CCAGATGTGA GCTCGTGATG ACCCAGACTC CA 32

( 2 ) INFORMATION FOR SEQ ID NO:27:

( i ) SEQUENCE CHARACTERISTICS:
        ( A ) LENGTH: 140 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

AACCTGCACC GTCTCCGGTT TCTCCCTGAC GAGCTATAGT GTACACTGGG TCCGTCAGCC 60

GCCGGGTAAA GGTCTAGAAT GGCTGGGTGT AATATGGGCT AGTGGAGGCA CAGATTATAA 120

TTCGGCTCTC ATGTCCCGTC 140

( 2 ) INFORMATION FOR SEQ ID NO:28:

( i ) SEQUENCE CHARACTERISTICS:
        ( A ) LENGTH: 149 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

```
ATATCGACAG ACGGGACATG AGAGCCGAAT TATAATCTGT GCCTCCACTA GCCCATATTA      60

CACCCAGCCA TTCTAGACCT TTACCCGGCG GCTGACGGAC CCAGTGTACA CTATAGCTCG     120

TCAGGGAGAA ACCGGAGACG GTGCAGGTT                                       149
```

( 2 ) INFORMATION FOR SEQ ID NO:29:

( i ) SEQUENCE CHARACTERISTICS:
        ( A ) LENGTH: 139 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

```
TGTCGATATC CAAAGACACC TCCCGTAACC AGGTTGTTCT GACCATGACT AACATGGACC      60

CGGTTGACAC CGCTACCTAC TACTGCGCTC GAGATCCCCC TTCTTCCTTA CTACGGCTTG     120

ACTACTGGGG TCGTGGTAC                                                  139
```

( 2 ) INFORMATION FOR SEQ ID NO:30:

( i ) SEQUENCE CHARACTERISTICS:
        ( A ) LENGTH: 126 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

```
CACGACCCCA GTAGTCAAGC CGTAGTAAGG AAGAAGGGGG ATCTCGAGCG CAGTAGTAGG      60

TAGCGGTGTC AACCGGGTCC ATGTTAGTCA TGGTCAGAAC AACCTGGTTA CGGGAGGTGT     120

CTTTGG                                                                126
```

( 2 ) INFORMATION FOR SEQ ID NO:31:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

```
CTCAGAGTCT GTTAAACAGT GGAAATCAAA AGAACTACTT GGCCTGGTAT CAGCAGAAAC      60

CCGGGCAGCC TCCTAAGTTG CTCATTTACG GGGCGTCGAC TAGGGAATCT GGGTAC         117
```

( 2 ) INFORMATION FOR SEQ ID NO:32:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

```
CCCAGATTCC CTAGTCGACG CCCCGTAAAT GAGCAACTTA GGAGGCTGCC CGGGTTTCTG      60

CTGATACCAG GCCAAGTAGT TCTTTTGATT TCCACTGTTT AACAGACTCT GAGAGCT        117
```

( 2 ) INFORMATION FOR SEQ ID NO:33:

( i ) SEQUENCE CHARACTERISTICS:
        ( A ) LENGTH: 102 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

```
GCTGAAGATG  TGGCAGTATA  CTACTGTCAG  AATGTTCATA  GTTTTCCATT  CACGTTCGGC      60
GGAGGGACCA  AGTTGGAGAT  CAAACGTACT  GTGGCGGCGC  CA                         102
```

( 2 ) INFORMATION FOR SEQ ID NO:34:

( i ) SEQUENCE CHARACTERISTICS:
        ( A ) LENGTH: 111 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

```
AGCTTGGCGC  CGCCACAGTA  CGTTTGATCT  CCAACTTGGT  CCCTCCGCCG  AACGTGAATG      60
GAAAACTATG  AACATTCTGA  CAGTAGTATA  CTGCCACATC  TTCAGCCTGC  A              111
```

( 2 ) INFORMATION FOR SEQ ID NO:35:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

```
ATGGTGTTGC  AGACCCAGGT  CTTCATTTCT  CTGTTGCTCT  GGATCTCTGG  TGCCTACGGG      60
CAGGTTCAAC  TGAAAGAGTC  AG                                                  82
```

( 2 ) INFORMATION FOR SEQ ID NO:36:

( i ) SEQUENCE CHARACTERISTICS:
        ( A ) LENGTH: 89 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

```
GTCCTGACTC  TTTCAGTTGA  ACCTGCCCGT  AGGCACCAGA  GATCCAGAGC  AACAGAGAAA      60
TGAAGACCTG  GGTCTGCAAC  ACCATGTTG                                           89
```

( 2 ) INFORMATION FOR SEQ ID NO:37:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

CAAGGCACCA CTCTCACAGT CTCCTCAGCT AGTACGAAGG GCCCA    45

( 2 ) INFORMATION FOR SEQ ID NO:38:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:38:

AGCTTGGGCC CTTCGTACTA GCTGAGGAGA CTGTGAGTGG TGC    43

( 2 ) INFORMATION FOR SEQ ID NO:39:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:39:

ATCGTGATGA CCCAGTCTCC ATCCTCCC    28

( 2 ) INFORMATION FOR SEQ ID NO:40:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:40:

TCAGGGAGGA TGGAGACTGG GTCATCACGA T    31

( 2 ) INFORMATION FOR SEQ ID NO:41:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:41:

TCGGGGACA GAGTTGGAAA TAAAACGTAC TGTGGCGGCG CCA    43

( 2 ) INFORMATION FOR SEQ ID NO:42:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:42:

AGCTTGGCGC CGCCACAGTA CGTTTTATTT CCAACTCTGT CC    42

( 2 ) INFORMATION FOR SEQ ID NO:43:

( i ) SEQUENCE CHARACTERISTICS:
   ( A ) LENGTH: 26 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:43:

CTAGCCACCA CCACCACCAC CACTAA 26

( 2 ) INFORMATION FOR SEQ ID NO:44:

( i ) SEQUENCE CHARACTERISTICS:
       ( A ) LENGTH: 26 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:44:

CTAGTTAGTG GTGGTGGTGG TGGTGG 26

( 2 ) INFORMATION FOR SEQ ID NO:45:

( i ) SEQUENCE CHARACTERISTICS:
       ( A ) LENGTH: 113 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO:45:

```
Glu Leu Val Met Thr Gln Ser Pro Ser Ser Leu Ser Val Ser Ala Gly
 1               5                  10                  15
Glu Lys Val Thr Met Ser Cys Lys Ser Ser Gln Ser Leu Leu Asn Ser
                20                  25                  30
Gly Asn Gln Lys Asn Tyr Leu Ala Trp Tyr Gln Gln Lys Pro Gly Gln
            35                  40                  45
Pro Pro Lys Leu Leu Ile Tyr Gly Ala Ser Thr Arg Glu Ser Gly Val
50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Ala Val Tyr Tyr Cys Gln Asn
                85                  90                  95
Asp His Ser Tyr Pro Phe Thr Phe Gly Ser Gly Thr Lys Leu Glu Ile
            100                 105                 110
Lys
```

( 2 ) INFORMATION FOR SEQ ID NO:46:

( i ) SEQUENCE CHARACTERISTICS:
       ( A ) LENGTH: 113 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO:46:

```
Glu Leu Val Met Thr Gln Ser Pro Ser Ser Leu Ser Val Ser Ala Gly
 1               5                  10                  15
Glu Lys Val Thr Met Ser Cys Lys Ser Ser Gln Ser Leu Leu Asn Ser
```

```
              20                    25                    30
    Gly Asn Gln Lys Asn Tyr Leu Ala Trp Tyr Gln Gln Lys Pro Gly Gln
            35                40                  45
    Pro Pro Lys Leu Leu Ile Tyr Gly Ala Ser Thr Arg Glu Ser Gly Val
        50                  55                60
    Pro Asp Arg Phe Thr Gly Ser Gly Ser Gly Thr Asp Phe Thr Leu Thr
    65                      70                  75                  80
    Ile Ser Ser Val Gln Ala Glu Asp Leu Ala Val Tyr Tyr Cys Gln Asn
                    85                  90                  95
    Asp Tyr Ser Tyr Pro Phe Thr Phe Gly Ser Gly Thr Lys Leu Glu Ile
                    100                 105                 110
    Lys
```

(2) INFORMATION FOR SEQ ID NO:47:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:47:

```
    Gln Asn Asp His Ser Tyr Pro Phe Thr
    1               5
```

(2) INFORMATION FOR SEQ ID NO:48:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:48:

```
    Gln Asn Asp Tyr Ser Tyr Pro Phe Thr
    1               5
```

(2) INFORMATION FOR SEQ ID NO:49:

( i ) SEQUENCE CHARACTERISTICS:
        ( A ) LENGTH: 6285 base pairs
        ( B ) TYPE: nucleic acid
        ( C ) STRANDEDNESS: double
        ( D ) TOPOLOGY: circular ( i i ) MOLECULE TYPE: DNA (genomic)

( x i ) SEQUENCE DESCRIPTION: SEQ ID NO:49:

```
GACGTCGCGG CCGCTCTAGG CCTCCAAAAA AGCCTCCTCA CTACTTCTGG AATAGCTCAG      60
AGGCCGAGGC GGCCTCGGCC TCTGCATAAA TAAAAAAAAT TAGTCAGCCA TGCATGGGGC     120
GGAGAATGGG CGGAACTGGG CGGAGTTAGG GGCGGGATGG GCGGAGTTAG GGGCGGGACT     180
ATGGTTGCTG ACTAATTGAG ATGCATGCTT TGCATACTTC TGCCTGCTGG GGAGCCTGGG     240
GACTTTCCAC ACCTGGTTGC TGACTAATTG AGATGCATGC TTTGCATACT TCTGCCTGCT     300
GGGGAGCCTG GGGACTTTCC ACACCCTAAC TGACACACAT TCCACAGAAT TAATTCCCGG     360
GGATCGATCC GTCGACGTAC GACTAGTTAT TAATAGTAAT CAATTACGGG TCATTAGTT     420
CATAGCCCAT ATATGGAGTT CCGCGTTACA TAACTTACGG TAAATGGCCC GCCTGGCTGA     480
```

-continued

| | | | | | |
|---|---|---|---|---|---|
| CCGCCCAACG | ACCCCCGCCC | ATTGACGTCA | ATAATGACGT | ATGTTCCCAT | AGTAACGCCA | 540 |
| ATAGGGACTT | TCCATTGACG | TCAATGGGTG | GACTATTTAC | GGTAAACTGC | CCACTTGGCA | 600 |
| GTACATCAAG | TGTATCATAT | GCCAAGTACG | CCCCCTATTG | ACGTCAATGA | CGGTAAATGG | 660 |
| CCCGCCTGGC | ATTATGCCCA | GTACATGACC | TTATGGGACT | TTCCTACTTG | GCAGTACATC | 720 |
| TACGTATTAG | TCATCGCTAT | TACCATGGTG | ATGCGGTTTT | GGCAGTACAT | CAATGGGCGT | 780 |
| GGATAGCGGT | TTGACTCACG | GGGATTTCCA | AGTCTCCACC | CCATTGACGT | CAATGGGAGT | 840 |
| TTGTTTTGGC | ACCAAAATCA | ACGGGACTTT | CCAAAATGTC | GTAACAACTC | CGCCCCATTG | 900 |
| ACGCAAATGG | GCGGTAGGCG | TGTACGGTGG | GAGGTCTATA | TAAGCAGAGC | TGGGTACGTG | 960 |
| AACCGTCAGA | TCGCCTGGAG | ACGCCATCGA | ATTCGAGGAC | GCCAGCAACA | TGGTGTTGCA | 1020 |
| GACCCAGGTC | TTCATTTCTC | TGTTGCTCTG | GATCTCTGGT | GCCTACGGGC | AGGTTACCCT | 1080 |
| GCGTGAATCC | GGTCCGGCAC | TAGTTAAACC | GACCAGACC | CTGACGTTAA | CCTGCACCGT | 1140 |
| CTCCGGTTTC | TCCCTGACGA | GCTATAGTGT | ACACTGGGTC | CGTCAGCCGC | CGGGTAAAGG | 1200 |
| TCTAGAATGG | CTGGGTGTAA | TATGGGCTAG | TGGAGGCACA | GATTATAATT | CGGCTCTCAT | 1260 |
| GTCCGTCTG | TCGATATCCA | AAGACACCTC | CCGTAACCAG | GTTGTTCTGA | CCATGACTAA | 1320 |
| CATGGACCCG | GTTGACACCG | CTACCTACTA | CTGCGCTCGA | GATCCCCCTT | CTTCCTTACT | 1380 |
| ACGGCTTGAC | TACTGGGGTC | GTGGTACCCC | AGTTACCGTG | AGCTCAGCTA | GTACCAAGGG | 1440 |
| CCCATCGGTC | TTCCCCCTGG | CACCCTCCTC | CAAGAGCACC | TCTGGGGGCA | CAGCGGCCCT | 1500 |
| GGGCTGCCTG | GTCAAGGACT | ACTTCCCCGA | ACCGGTGACG | GTGTCGTGGA | ACTCAGGCGC | 1560 |
| CCTGACCAGC | GGCGTGCACA | CCTTCCCGGC | TGTCCTACAG | TCCTCAGGAC | TCTACTCCCT | 1620 |
| CAGCAGCGTG | GTGACCGTGC | CCTCCAGCAG | CTTGGGCACC | CAGACCTACA | TCTGCAACGT | 1680 |
| GAATCACAAG | CCCAGCAACA | CCAAGGTGGA | CAAGAGAGTT | GAGCCCAAAT | CTTGTGACAA | 1740 |
| AACTCACACA | TGCCCACCGT | GCCCAGCACC | TGAACTCCTG | GGGGACCGT | CAGTCTTCCT | 1800 |
| CTTCCCCCCA | AAACCCAAGG | ACACCCTCAT | GATCTCCCGG | ACCCCTGAGG | TCACATGCGT | 1860 |
| GGTGGTGGAC | GTGAGCCACG | AAGACCCTGA | GGTCAAGTTC | AACTGGTACG | TGGACGGCGT | 1920 |
| GGAGGTGCAT | AATGCCAAGA | CAAAGCCGCG | GGAGGAGCAG | TACAACAGCA | CGTACCGTGT | 1980 |
| GGTCAGCGTC | CTCACCGTCC | TGCACCAGGA | CTGGCTGAAT | GGCAAGGAGT | ACAAGTGCAA | 2040 |
| GGTCTCCAAC | AAAGCCCTCC | CAGCCCCCAT | CGAGAAAACC | ATCTCCAAAG | CCAAAGGGCA | 2100 |
| GCCCCGAGAA | CCACAGGTGT | ACACCCTGCC | CCCATCCCGG | GAGGAGATGA | CCAAGAACCA | 2160 |
| GGTCAGCCTG | ACCTGCCTGG | TCAAAGGCTT | CTATCCCAGC | GACATCGCCG | TGGAGTGGGA | 2220 |
| GAGCAATGGG | CAGCCGGAGA | ACAACTACAA | GACCACGCCT | CCCGTGCTGG | ACTCCGACGG | 2280 |
| CTCCTTCTTC | CTCTATAGCA | AGCTCACCGT | GGACAAGAGC | AGGTGGCAGC | AGGGGAACGT | 2340 |
| CTTCTCATGC | TCCGTGATGC | ATGAGGCTCT | GCACAACCAC | TACACGCAGA | AGAGCCTCTC | 2400 |
| CCTGTCTCCG | GGTAAGTGAG | TGTAGTCTAG | ATCTACGTAT | GATCAGCCTC | GACTGTGCCT | 2460 |
| TCTAGTTGCC | AGCCATCTGT | TGTTTGCCCC | TCCCCCGTGC | CTTCCTTGAC | CCTGGAAGGT | 2520 |
| GCCACTCCCA | CTGTCCTTTC | CTAATAAAAT | GAGGAAATTG | CATCGCATTG | TCTGAGTAGG | 2580 |
| TGTCATTCTA | TTCTGGGGGG | TGGGGTGGGG | CAGGACAGCA | AGGGGGAGGA | TTGGGAAGAC | 2640 |
| AATAGCAGGC | ATGCTGGGGA | TGCGGTGGGC | TCTATGGAAC | CAGCTGGGGC | TCGACAGCGC | 2700 |
| TGGATCTCCC | GATCCCAGC | TTTGCTTCTC | AATTTCTTAT | TTGCATAATG | AGAAAAAAAG | 2760 |
| GAAAATTAAT | TTTAACACCA | ATTCAGTAGT | TGATTGAGCA | AATGCGTTGC | CAAAAAGGAT | 2820 |
| GCTTTAGAGA | CAGTGTTCTC | TGCACAGATA | AGGACAAACA | TTATTCAGAG | GGAGTACCCA | 2880 |

```
GAGCTGAGAC  TCCTAAGCCA  GTGAGTGGCA  CAGCATTCTA  GGGAGAAATA  TGCTTGTCAT   2940
CACCGAAGCC  TGATTCCGTA  GAGCCACACC  TTGGTAAGGG  CCAATCTGCT  CACACAGGAT   3000
AGAGAGGGCA  GGAGCCAGGG  CAGAGCATAT  AAGGTGAGGT  AGGATCAGTT  GCTCCTCACA   3060
TTTGCTTCTG  ACATAGTTGT  GTTGGGAGCT  TGGATAGCTT  GGACAGCTCA  GGGCTGCGAT   3120
TTCGCGCCAA  ACTTGACGGC  AATCCTAGCG  TGAAGGCTGG  TAGGATTTTA  TCCCCGCTGC   3180
CATCATGGTT  CGACCATTGA  ACTGCATCGT  CGCCGTGTCC  CAAAATATGG  GGATTGGCAA   3240
GAACGGAGAC  CTACCCTGGC  CTCCGCTCAG  GAACGAGTTC  AAGTACTTCC  AAAGAATGAC   3300
CACAACCTCT  TCAGTGGAAG  GTAAACAGAA  TCTGGTGATT  ATGGGTAGGA  AAACCTGGTT   3360
CTCCATTCCT  GAGAAGAATC  GACCTTTAAA  GGACAGAATT  AATATAGTTC  TCAGTAGAGA   3420
ACTCAAAGAA  CCACCACGAG  GAGCTCATTT  TCTTGCCAAA  AGTTTGGATG  ATGCCTTAAG   3480
ACTTATTGAA  CAACCGGAAT  TGGCAAGTAA  AGTAGACATG  GTTGGATAG   TCGGAGGCAG   3540
TTCTGTTTAC  CAGGAAGCCA  TGAATCAACC  AGGCCACCTT  AGACTCTTTG  TGACAAGGAT   3600
CATGCAGGAA  TTTGAAAGTG  ACACGTTTTT  CCCAGAAATT  GATTTGGGGA  AATATAAACT   3660
TCTCCCAGAA  TACCCAGGCG  TCCTCTCTGA  GGTCCAGGAG  GAAAAAGGCA  TCAAGTATAA   3720
GTTGAAGTC   TACGAGAAGA  AAGACTAACA  GGAAGATGCT  TTCAAGTTCT  CTGCTCCCCT   3780
CCTAAAGCTA  TGCATTTTTA  TAAGACCATG  GGACTTTTGC  TGGCTTTAGA  TCAGCCTCGA   3840
CTGTGCCTTC  TAGTTGCCAG  CCATCTGTTG  TTTGCCCCTC  CCCCGTGCCT  TCCTTGACCC   3900
TGGAAGGTGC  CACTCCCACT  GTCCTTTCCT  AATAAAATGA  GGAAATTGCA  TCGCATTGTC   3960
TGAGTAGGTG  TCATTCTATT  CTGGGGGGTG  GGGTGGGGCA  GGACAGCAAG  GGGGAGGATT   4020
GGGAAGACAA  TAGCAGGCAT  GCTGGGGATG  CGGTGGGCTC  TATGGAACCA  GCTGGGGCTC   4080
GATCGAGTGT  ATGACTGCGG  CCGCGATCCC  GTCGAGAGCT  TGGCGTAATC  ATGGTCATAG   4140
CTGTTTCCTG  TGTGAAATTG  TTATCCGCTC  ACAATTCCAC  ACAACATACG  AGCCGGAAGC   4200
ATAAAGTGTA  AAGCCTGGGG  TGCCTAATGA  GTGAGCTAAC  TCACATTAAT  TGCGTTGCGC   4260
TCACTGCCCG  CTTTCCAGTC  GGGAAACCTG  TCGTGCCAGC  TGCATTAATG  AATCGGCCAA   4320
CGCGCGGGGA  GAGGCGGTTT  GCGTATTGGG  CGCTCTTCCG  CTTCCTCGCT  CACTGACTCG   4380
CTGCGCTCGG  TCGTTCGGCT  GCGGCGAGCG  GTATCAGCTC  ACTCAAAGGC  GGTAATACGG   4440
TTATCCACAG  AATCAGGGGA  TAACGCAGGA  AAGAACATGT  GAGCAAAAGG  CCAGCAAAAG   4500
GCCAGGAACC  GTAAAAAGGC  CGCGTTGCTG  GCGTTTTTCC  ATAGGCTCCG  CCCCCCTGAC   4560
GAGCATCACA  AAAATCGACG  CTCAAGTCAG  AGGTGGCGAA  ACCCGACAGG  ACTATAAAGA   4620
TACCAGGCGT  TTCCCCCTGG  AAGCTCCCTC  GTGCGCTCTC  CTGTTCCGAC  CCTGCCGCTT   4680
ACCGGATACC  TGTCCGCCTT  TCTCCCTTCG  GGAAGCGTGG  CGCTTTCTCA  ATGCTCACGC   4740
TGTAGGTATC  TCAGTTCGGT  GTAGGTCGTT  CGCTCCAAGC  TGGGCTGTGT  GCACGAACCC   4800
CCCGTTCAGC  CCGACCGCTG  CGCCTTATCC  GGTAACTATC  GTCTTGAGTC  CAACCCGGTA   4860
AGACACGACT  TATCGCCACT  GGCAGCAGCC  ACTGGTAACA  GGATTAGCAG  AGCGAGGTAT   4920
GTAGGCGGTG  CTACAGAGTT  CTTGAAGTGG  TGGCCTAACT  ACGGCTACAC  TAGAAGGACA   4980
GTATTTGGTA  TCTGCGCTCT  GCTGAAGCCA  GTTACCTTCG  GAAAAGAGT   TGGTAGCTCT   5040
TGATCCGGCA  AACAAACCAC  CGCTGGTAGC  GGTGGTTTTT  TTGTTTGCAA  GCAGCAGATT   5100
ACGCGCAGAA  AAAAGGATC   TCAAGAAGAT  CCTTTGATCT  TTTCTACGGG  GTCTGACGCT   5160
CAGTGGAACG  AAAACTCACG  TTAAGGGATT  TTGGTCATGA  GATTATCAAA  AAGGATCTTC   5220
ACCTAGATCC  TTTTAAATTA  AAAATGAAGT  TTAAATCAA   TCTAAAGTAT  ATATGAGTAA   5280
```

-continued

| | | | | | | |
|---|---|---|---|---|---|---|
| ACTTGGTCTG | ACAGTTACCA | ATGCTTAATC | AGTGAGGCAC | CTATCTCAGC | GATCTGTCTA | 5340 |
| TTTCGTTCAT | CCATAGTTGC | CTGACTCCCC | GTCGTGTAGA | TAACTACGAT | ACGGGAGGGC | 5400 |
| TTACCATCTG | GCCCCAGTGC | TGCAATGATA | CCGCGAGACC | CACGCTCACC | GGCTCCAGAT | 5460 |
| TTATCAGCAA | TAAACCAGCC | AGCCGGAAGG | GCCGAGCGCA | GAAGTGGTCC | TGCAACTTTA | 5520 |
| TCCGCCTCCA | TCCAGTCTAT | TAATTGTTGC | CGGGAAGCTA | GAGTAAGTAG | TTCGCCAGTT | 5580 |
| AATAGTTTGC | GCAACGTTGT | TGCCATTGCT | ACAGGCATCG | TGGTGTCACG | CTCGTCGTTT | 5640 |
| GGTATGGCTT | CATTCAGCTC | CGGTTCCCAA | CGATCAAGGC | GAGTTACATG | ATCCCCATG | 5700 |
| TTGTGCAAAA | AAGCGGTTAG | CTCCTTCGGT | CCTCCGATCG | TTGTCAGAAG | TAAGTTGGCC | 5760 |
| GCAGTGTTAT | CACTCATGGT | TATGGCAGCA | CTGCATAATT | CTCTTACTGT | CATGCCATCC | 5820 |
| GTAAGATGCT | TTTCTGTGAC | TGGTGAGTAC | TCAACCAAGT | CATTCTGAGA | ATAGTGTATG | 5880 |
| CGGCGACCGA | GTTGCTCTTG | CCCGGCGTCA | ATACGGGATA | ATACCGCGCC | ACATAGCAGA | 5940 |
| ACTTTAAAAG | TGCTCATCAT | TGGAAAACGT | TCTTCGGGGC | GAAAACTCTC | AAGGATCTTA | 6000 |
| CCGCTGTTGA | GATCCAGTTC | GATGTAACCC | ACTCGTGCAC | CCAACTGATC | TTCAGCATCT | 6060 |
| TTTACTTTCA | CCAGCGTTTC | TGGGTGAGCA | AAAACAGGAA | GGCAAAATGC | CGCAAAAAAG | 6120 |
| GGAATAAGGG | CGACACGGAA | ATGTTGAATA | CTCATACTCT | TCCTTTTTCA | ATATTATTGA | 6180 |
| AGCATTTATC | AGGGTTATTG | TCTCATGAGC | GGATACATAT | TTGAATGTAT | TTAGAAAAAT | 6240 |
| AAACAAATAG | GGGTTCCGCG | CACATTTCCC | CGAAAAGTGC | CACCT | | 6285 |

( 2 ) INFORMATION FOR SEQ ID NO:50:

( i ) SEQUENCE CHARACTERISTICS:
        ( A ) LENGTH: 5703 base pairs
        ( B ) TYPE: nucleic acid
        ( C ) STRANDEDNESS: double
        ( D ) TOPOLOGY: circular ( i i ) MOLECULE TYPE: DNA (genomic)

( x i ) SEQUENCE DESCRIPTION: SEQ ID NO:50:

| | | | | | | |
|---|---|---|---|---|---|---|
| GACGTCGCGG | CCGCTCTAGG | CCTCCAAAAA | AGCCTCCTCA | CTACTTCTGG | AATAGCTCAG | 60 |
| AGGCCGAGGC | GGCCTCGGCC | TCTGCATAAA | TAAAAAAAAT | TAGTCAGCCA | TGCATGGGGC | 120 |
| GGAGAATGGG | CGGAACTGGG | CGGAGTTAGG | GGCGGGATGG | GCGGAGTTAG | GGGCGGGACT | 180 |
| ATGGTTGCTG | ACTAATTGAG | ATGCATGCTT | TGCATACTTC | TGCCTGCTGG | GGAGCCTGGG | 240 |
| GACTTTCCAC | ACCTGGTTGC | TGACTAATTG | AGATGCATGC | TTTGCATACT | TCTGCCTGCT | 300 |
| GGGGAGCCTG | GGGACTTTCC | ACACCCTAAC | TGACACACAT | TCCACAGAAT | TAATTCCCGG | 360 |
| GGATCGATCC | GTCGACGTAC | GACTAGTTAT | TAATAGTAAT | CAATTACGGG | GTCATTAGTT | 420 |
| CATAGCCCAT | ATATGGAGTT | CCGCGTTACA | TAACTTACGG | TAAATGGCCC | GCCTGGCTGA | 480 |
| CCGCCCAACG | ACCCCCGCCC | ATTGACGTCA | ATAATGACGT | ATGTTCCCAT | AGTAACGCCA | 540 |
| ATAGGGACTT | TCCATTGACG | TCAATGGGTG | GACTATTTAC | GGTAAACTGC | CCACTTGGCA | 600 |
| GTACATCAAG | TGTATCATAT | GCCAAGTACG | CCCCCTATTG | ACGTCAATGA | CGGTAAATGG | 660 |
| CCCGCCTGGC | ATTATGCCCA | GTACATGACC | TTATGGGACT | TTCCTACTTG | GCAGTACATC | 720 |
| TACGTATTAG | TCATCGCTAT | TACCATGGTG | ATGCGGTTTT | GGCAGTACAT | CAATGGGCGT | 780 |
| GGATAGCGGT | TTGACTCACG | GGGATTTCCA | AGTCTCCACC | CCATTGACGT | CAATGGGAGT | 840 |
| TTGTTTTGGC | ACCAAAATCA | ACGGGACTTT | CCAAAATGTC | GTAACAACTC | CGCCCCATTG | 900 |
| ACGCAAATGG | GCGGTAGGCG | TGTACGGTGG | GAGGTCTATA | TAAGCAGAGC | TGGGTACGTG | 960 |
| AACCGTCAGA | TCGCCTGGAG | ACGCCATCGA | ATTCATTGAT | AGGATCCAGC | AAGATGGTGT | 1020 |

| | | | | | |
|---|---|---|---|---|---|
| TGCAGACCCA | GGTCTTCATT | TCTCTGTTGC | TCTGGATCTC | TGGTGCCTAC | GGGGATATCG | 1080
| TGATGACCCA | GTCTCCAGAC | TCGCTAGCTG | TGTCTCTGGG | CGAGAGGGCC | ACCATCAACT | 1140
| GCAAGAGCTC | TCAGAGTCTG | TTAAACAGTG | GAAATCAAAA | GAACTACTTG | GCCTGGTATC | 1200
| AGCAGAAACC | CGGGCAGCCT | CCTAAGTTGC | TCATTTACGG | GGCGTCGACT | AGGGAATCTG | 1260
| GGGTACCTGA | CCGATTCAGT | GGCAGCGGGT | CTGGGACAGA | TTTCACTCTC | ACCATCAGCA | 1320
| GCCTGCAGGC | TGAAGATGTG | GCAGTATACT | ACTGTCAGAA | TGTTCATAGT | TTTCCATTCA | 1380
| CGTTCGGCGG | AGGGACCAAG | TTGGAGATCA | AACGTACTGT | GGCGGCGCCA | TCTGTCTTCA | 1440
| TCTTCCCGCC | ATCTGATGAG | CAGTTGAAAT | CTGGAACTGC | CTCTGTTGTG | TGCCTGCTGA | 1500
| ATAACTTCTA | TCCCAGAGAG | GCCAAAGTAC | AGTGGAAGGT | GGATAACGCC | CTCCAATCGG | 1560
| GTAACTCCCA | GGAGAGTGTC | ACAGAGCAGG | ACAGCAAGGA | CAGCACCTAC | AGCCTCAGCA | 1620
| GCACCCTGAC | GCTGAGCAAA | GCAGACTACG | AGAAACACAA | AGTCTACGCC | TGCGAAGTCA | 1680
| CCCATCAGGG | CCTGAGCTCG | CCCGTCACAA | AGAGCTTCAA | CAGGGGAGAG | TGTTAATTCT | 1740
| AGATCCGTTA | TCTACGTATG | ATCAGCCTCG | ACTGTGCCTT | CTAGTTGCCA | GCCATCTGTT | 1800
| GTTTGCCCCT | CCCCCGTGCC | TTCCTTGACC | CTGGAAGGTG | CCACTCCCAC | TGTCCTTTCC | 1860
| TAATAAAATG | AGGAAATTGC | ATCGCATTGT | CTGAGTAGGT | GTCATTCTAT | TCTGGGGGGT | 1920
| GGGGTGGGGC | AGGACAGCAA | GGGGGAGGAT | TGGGAAGACA | ATAGCAGGCA | TGCTGGGGAT | 1980
| GCGGTGGGCT | CTATGGAACC | AGCTGGGGCT | CGACAGCTCG | AGCTAGCTTT | GCTTCTCAAT | 2040
| TTCTTATTTG | CATAATGAGA | AAAAAAGGAA | AATTAATTTT | AACACCAATT | CAGTAGTTGA | 2100
| TTGAGCAAAT | GCGTTGCCAA | AAAGGATGCT | TTAGAGACAG | TGTTCTCTGC | ACAGATAAGG | 2160
| ACAAACATTA | TTCAGAGGGA | GTACCCAGAG | CTGAGACTCC | TAAGCCAGTG | AGTGGCACAG | 2220
| CATTCTAGGG | AGAAATATGC | TTGTCATCAC | CGAAGCCTGA | TTCCGTAGAG | CCACACCTTG | 2280
| GTAAGGGCCA | ATCTGCTCAC | ACAGGATAGA | GAGGGCAGGA | GCCAGGGCAG | AGCATATAAG | 2340
| GTGAGGTAGG | ATCAGTTGCT | CCTCACATTT | GCTTCTGACA | TAGTTGTGTT | GGGAGCTTGG | 2400
| ATCGATCCAC | CATGGTTGAA | CAAGATGGAT | TGCACGCAGG | TTCTCCGGCC | GCTTGGGTGG | 2460
| AGAGGCTATT | CGGCTATGAC | TGGGCACAAC | AGACAATCGG | CTGCTCTGAT | GCCGCCGTGT | 2520
| TCCGGCTGTC | AGCGCAGGGG | CGCCCGGTTC | TTTTTGTCAA | GACCGACCTG | TCCGGTGCCC | 2580
| TGAATGAACT | GCAGGACGAG | GCAGCGCGGC | TATCGTGGCT | GGCCACGACG | GGCGTTCCTT | 2640
| GCGCAGCTGT | GCTCGACGTT | GTCACTGAAG | CGGGAAGGGA | CTGGCTGCTA | TTGGGCGAAG | 2700
| TGCCGGGGCA | GGATCTCCTG | TCATCTCACC | TTGCTCCTGC | CGAGAAAGTA | TCCATCATGG | 2760
| CTGATGCAAT | GCGGCGGCTG | CATACGCTTG | ATCCGGCTAC | CTGCCCATTC | GACCACCAAG | 2820
| CGAAACATCG | CATCGAGCGA | GCACGTACTC | GGATGGAAGC | CGGTCTTGTC | GATCAGGATG | 2880
| ATCTGGACGA | AGAGCATCAG | GGGCTCGCGC | CAGCCGAACT | GTTCGCCAGG | CTCAAGGCGC | 2940
| GCATGCCCGA | CGGCGAGGAT | CTCGTCGTGA | CCCATGGCGA | TGCCTGCTTG | CCGAATATCA | 3000
| TGGTGGAAAA | TGGCCGCTTT | TCTGGATTCA | TCGACTGTGG | CCGGCTGGGT | GTGGCGGACC | 3060
| GCTATCAGGA | CATAGCGTTG | GCTACCCGTG | ATATTGCTGA | AGAGCTTGGC | GGCGAATGGG | 3120
| CTGACCGCTT | CCTCGTGCTT | TACGGTATCG | CCGCTCCCGA | TTCGCAGCGC | ATCGCCTTCT | 3180
| ATCGCCTTCT | TGACGAGTTC | TTCTGAGCGG | GACTCTGGGG | TTCGAAATGA | CCGACCAAGC | 3240
| GACGCCCAAC | CTGCCATCAC | GAGATTTCGA | TTCCACCGCC | GCCTTCTATG | AAAGGTTGGG | 3300
| CTTCGGAATC | GTTTTCCGGG | ACGCCGGCTG | GATGATCCTC | CAGCGCGGGG | ATCTCATGCT | 3360
| GGAGTTCTTC | GCCCACCCCA | ACTTGTTTAT | TGCAGCTTAT | AATGGTTACA | AATAAAGCAA | 3420

```
TAGCATCACA  AATTTCACAA  ATAAAGCATT  TTTTTCACTG  CATTCTAGTT  GTGGTTTGTC  3480
CAAACTCATC  AATGTATCTT  ATCATGTCTG  GATCGCGGCC  GCGATCCCGT  CGAGAGCTTG  3540
GCGTAATCAT  GGTCATAGCT  GTTTCCTGTG  TGAAATTGTT  ATCCGCTCAC  AATTCCACAC  3600
AACATACGAG  CCGGAAGCAT  AAAGTGTAAA  GCCTGGGGTG  CCTAATGAGT  GAGCTAACTC  3660
ACATTAATTG  CGTTGCGCTC  ACTGCCCGCT  TTCCAGTCGG  GAAACCTGTC  GTGCCAGCTG  3720
CATTAATGAA  TCGGCCAACG  CGCGGGGAGA  GGCGGTTTGC  GTATTGGGCG  CTCTTCCGCT  3780
TCCTCGCTCA  CTGACTCGCT  GCGCTCGGTC  GTTCGGCTGC  GGCGAGCGGT  ATCAGCTCAC  3840
TCAAAGGCGG  TAATACGGTT  ATCCACAGAA  TCAGGGGATA  ACGCAGGAAA  GAACATGTGA  3900
GCAAAAGGCC  AGCAAAAGGC  CAGGAACCGT  AAAAAGGCCG  CGTTGCTGGC  GTTTTTCCAT  3960
AGGCTCCGCC  CCCCTGACGA  GCATCACAAA  AATCGACGCT  CAAGTCAGAG  GTGGCGAAAC  4020
CCGACAGGAC  TATAAAGATA  CCAGGCGTTT  CCCCCTGGAA  GCTCCCTCGT  GCGCTCTCCT  4080
GTTCCGACCC  TGCCGCTTAC  CGGATACCTG  TCCGCCTTTC  TCCCTTCGGG  AAGCGTGGCG  4140
CTTTCTCAAT  GCTCACGCTG  TAGGTATCTC  AGTTCGGTGT  AGGTCGTTCG  CTCCAAGCTG  4200
GGCTGTGTGC  ACGAACCCCC  CGTTCAGCCC  GACCGCTGCG  CCTTATCCGG  TAACTATCGT  4260
CTTGAGTCCA  ACCCGGTAAG  ACACGACTTA  TCGCCACTGG  CAGCAGCCAC  TGGTAACAGG  4320
ATTAGCAGAG  CGAGGTATGT  AGGCGGTGCT  ACAGAGTTCT  TGAAGTGGTG  GCCTAACTAC  4380
GGCTACACTA  GAAGGACAGT  ATTTGGTATC  TGCGCTCTGC  TGAAGCCAGT  TACCTTCGGA  4440
AAAAGAGTTG  GTAGCTCTTG  ATCCGGCAAA  CAAACCACCG  CTGGTAGCGG  TGGTTTTTTT  4500
GTTTGCAAGC  AGCAGATTAC  GCGCAGAAAA  AAAGGATCTC  AAGAAGATCC  TTTGATCTTT  4560
TCTACGGGGT  CTGACGCTCA  GTGGAACGAA  AACTCACGTT  AAGGGATTTT  GGTCATGAGA  4620
TTATCAAAAA  GGATCTTCAC  CTAGATCCTT  TTAAATTAAA  AATGAAGTTT  TAAATCAATC  4680
TAAAGTATAT  ATGAGTAAAC  TTGGTCTGAC  AGTTACCAAT  GCTTAATCAG  TGAGGCACCT  4740
ATCTCAGCGA  TCTGTCTATT  TCGTTCATCC  ATAGTTGCCT  GACTCCCCGT  CGTGTAGATA  4800
ACTACGATAC  GGGAGGGCTT  ACCATCTGGC  CCCAGTGCTG  CAATGATACC  GCGAGACCCA  4860
CGCTCACCGG  CTCCAGATTT  ATCAGCAATA  AACCAGCCAG  CCGGAAGGGC  CGAGCGCAGA  4920
AGTGGTCCTG  CAACTTTATC  CGCCTCCATC  CAGTCTATTA  ATTGTTGCCG  GGAAGCTAGA  4980
GTAAGTAGTT  CGCCAGTTAA  TAGTTTGCGC  AACGTTGTTG  CCATTGCTAC  AGGCATCGTG  5040
GTGTCACGCT  CGTCGTTTGG  TATGGCTTCA  TTCAGCTCCG  GTTCCCAACG  ATCAAGGCGA  5100
GTTACATGAT  CCCCCATGTT  GTGCAAAAAA  GCGGTTAGCT  CCTTCGGTCC  TCCGATCGTT  5160
GTCAGAAGTA  AGTTGGCCGC  AGTGTTATCA  CTCATGGTTA  TGGCAGCACT  GCATAATTCT  5220
CTTACTGTCA  TGCCATCCGT  AAGATGCTTT  TCTGTGACTG  GTGAGTACTC  AACCAAGTCA  5280
TTCTGAGAAT  AGTGTATGCG  GCGACCGAGT  TGCTCTTGCC  CGGCGTCAAT  ACGGGATAAT  5340
ACCGCGCCAC  ATAGCAGAAC  TTTAAAAGTG  CTCATCATTG  GAAAACGTTC  TTCGGGGCGA  5400
AAACTCTCAA  GGATCTTACC  GCTGTTGAGA  TCCAGTTCGA  TGTAACCCAC  TCGTGCACCC  5460
AACTGATCTT  CAGCATCTTT  TACTTTCACC  AGCGTTTCTG  GGTGAGCAAA  AACAGGAAGG  5520
CAAAATGCCG  CAAAAAAGGG  AATAAGGGCG  ACACGGAAAT  GTTGAATACT  CATACTCTTC  5580
CTTTTTCAAT  ATTATTGAAG  CATTTATCAG  GGTTATTGTC  TCATGAGCGG  ATACATATTT  5640
GAATGTATTT  AGAAAAATAA  ACAAATAGGG  GTTCCGCGCA  CATTTCCCCG  AAAAGTGCCA  5700
CCT                                                                   5703
```

( 2 ) INFORMATION FOR SEQ ID NO:51:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

ATCCAAAGAC AACTCCCGTA ACCAGGTTGT TCTGACCATG ACTAACATGG ACCCGGTTGA    60

CACCGCTACC TACTACTGCG C    81

( 2 ) INFORMATION FOR SEQ ID NO:52:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:52:

TCGAGCGCAG TAGTAGGTAG CGGTGTCAAC CGGGTCCATG TTAGTCATGG TCAGAACAAC    60

CTGGTTACGG GAGTTGTCTT TGGAT    85

( 2 ) INFORMATION FOR SEQ ID NO:53:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:53:

AACCTGCACC GTCTCCGGTT TCTCCCTGAC GAGCTATAGT GTACACTGGA TCCGTCAGCC    60

GCCGGGTAAA GGT    73

( 2 ) INFORMATION FOR SEQ ID NO:54:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:54:

CTAGACCTTT ACCCGGCGGC TGACGGATCC AGTGTACACT ATAGCTCGTC AGGGAGAAAC    60

CGGAGACGGT GCAGGTT    77

( 2 ) INFORMATION FOR SEQ ID NO:55:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:55:

CTAGCTGTGT CAGCTGGCGA GAGGGCCACC ATCAACTGCA AGAGCT    46

( 2 ) INFORMATION FOR SEQ ID NO:56:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:56:

CTTGCAGTTG ATGGTGGCCC TCTCGCCAGC TGACACAG    38

( 2 ) INFORMATION FOR SEQ ID NO:57:

( i ) SEQUENCE CHARACTERISTICS:
        ( A ) LENGTH: 140 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:57:

TTCGAGGACG CCAGCAACAT GGTGTTGCAG ACCCAGGTCT TCATTTCTCT GTTGCTCTGG    60
ATCTCTGGTG CCTACGGGCA GGTCCAACTG CAGGAGAGCG GTCCAGGTCT TGTGAGACCT    120
AGCCAGACCC TGAGCCTGAC    140

( 2 ) INFORMATION FOR SEQ ID NO:58:

( i ) SEQUENCE CHARACTERISTICS:
        ( A ) LENGTH: 138 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:58:

GTGCCTCCAC TAGCCCATAT TACTCCAAGC CACTCTAGAC CTCGTCCAGG TGGCTGTCTC    60
ACCCAGTGTA CACTATAGCT GGTGAGGGAG AAGCCCGAGA CGGTGCAGGT CAGGCTCAGG    120
GTCTGGCTAG GTCTCACA    138

( 2 ) INFORMATION FOR SEQ ID NO:59:

( i ) SEQUENCE CHARACTERISTICS:
        ( A ) LENGTH: 143 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:59:

GGCTTGGAGT AATATGGGCT AGTGGAGGCA CAGATTATAA TTCGGCTCTC ATGTCCAGAC    60
TGAGTATACT GAAAGACAAC AGCAAGAACC AGGTCAGCCT GAGACTCAGC AGCGTGACAG    120
CCGCCGACAC CGCGGTCTAT TTC    143

( 2 ) INFORMATION FOR SEQ ID NO:60:

( i ) SEQUENCE CHARACTERISTICS:
        ( A ) LENGTH: 136 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:60:

| | | | | | |
|---|---|---|---|---|---|
| CCAGTGCCAA | GCTTGGGCCC | TTGGTGGAGG | CGCTCGAGAC | GGTGACCGTG | GTACCTTGTC | 60 |
| CCCAGTAGTC | AAGCCGTAGT | AAGGAAGAAG | GGGGATCTCG | AGCACAGAAA | TAGACCGCGG | 120 |
| TGTCGGCGGC | TGTCAC | | | | | 136 |

( 2 ) INFORMATION FOR SEQ ID NO:61:

( i ) SEQUENCE CHARACTERISTICS:
( A ) LENGTH: 357 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:61:

| | | | | | |
|---|---|---|---|---|---|
| CAGGTCCAAC | TGCAGGAGAG | CGGTCCAGGT | CTTGTGAGAC | CTAGCCAGAC | CCTGAGCCTG | 60 |
| ACCTGCACCG | TCTCGGGCTT | CTCCCTCACC | AGCTATAGTG | TACACTGGGT | GAGACAGCCA | 120 |
| CCTGGACGAG | GTCTAGAGTG | GCTTGGAGTA | ATATGGGCTA | GTGGAGGCAC | AGATTATAAT | 180 |
| TCGGCTCTCA | TGTCCAGACT | GAGTATACTG | AAAGACAACA | GCAAGAACCA | GGTCAGCCTG | 240 |
| AGACTCAGCA | GCGTGACAGC | CGCCGACACC | GCGGTCTATT | ACTGTGCTCG | GGATCCCCCT | 300 |
| TCTTCCTTAC | TACGGCTTGA | CTACTGGGGA | CAAGGTACCA | CGGTCACCGT | CTCGAGC | 357 |

( 2 ) INFORMATION FOR SEQ ID NO:62:

( i ) SEQUENCE CHARACTERISTICS:
( A ) LENGTH: 119 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:62:

| Gln | Val | Gln | Leu | Gln | Glu | Ser | Gly | Pro | Gly | Leu | Val | Arg | Pro | Ser | Gln |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Thr | Val | Ser | Gly | Phe | Ser | Leu | Thr | Ser | Tyr |
|---|---|---|---|---|---|---|---|---|---|---|---|---|---|---|---|
| | | | 20 | | | | | 25 | | | | | 30 | | |

| Ser | Val | His | Trp | Val | Arg | Gln | Pro | Pro | Gly | Arg | Gly | Leu | Glu | Trp | Leu |
|---|---|---|---|---|---|---|---|---|---|---|---|---|---|---|---|
| | | 35 | | | | | 40 | | | | | 45 | | | |

| Gly | Val | Ile | Trp | Ala | Ser | Gly | Gly | Thr | Asp | Tyr | Asn | Ser | Ala | Leu | Met |
|---|---|---|---|---|---|---|---|---|---|---|---|---|---|---|---|
| | 50 | | | | | 55 | | | | | 60 | | | | |

| Ser | Arg | Leu | Ser | Ile | Leu | Lys | Asp | Asn | Ser | Lys | Asn | Gln | Val | Ser | Leu |
|---|---|---|---|---|---|---|---|---|---|---|---|---|---|---|---|
| 65 | | | | | 70 | | | | | 75 | | | | | 80 |

| Arg | Leu | Ser | Ser | Val | Thr | Ala | Ala | Asp | Thr | Ala | Val | Tyr | Tyr | Cys | Ala |
|---|---|---|---|---|---|---|---|---|---|---|---|---|---|---|---|
| | | | | 85 | | | | | 90 | | | | | 95 | |

| Arg | Asp | Pro | Pro | Ser | Ser | Leu | Leu | Arg | Leu | Asp | Tyr | Trp | Gly | Gln | Gly |
|---|---|---|---|---|---|---|---|---|---|---|---|---|---|---|---|
| | | | 100 | | | | | 105 | | | | | 110 | | |

| Thr | Thr | Val | Thr | Val | Ser | Ser |
|---|---|---|---|---|---|---|
| | | 115 | | | | |

( 2 ) INFORMATION FOR SEQ ID NO:63:

( i ) SEQUENCE CHARACTERISTICS:
( A ) LENGTH: 28 base pairs ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:63:

AGGACGCCAG CAACATGGTG TTGCAGAC                                                    28

( 2 ) INFORMATION FOR SEQ ID NO:64:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:64:

TGCCAAGCTT GGGCCCTTGG TGGAGGCGCT CGAGAC                                            36

( 2 ) INFORMATION FOR SEQ ID NO:65:

( i ) SEQUENCE CHARACTERISTICS:
( A ) LENGTH: 121 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:65:

GACCATGATT ACGAATTCGT AGTCGGATAT CGTGATGACC AGAGCCCAA GCAGCCTGAG            60
CGCTAGCGTG GGTGACAGAG TGACCATCAC CTGTAAGAGC TCTCAGAGTC TGTTAAACAG          120
T                                                                                                                           121

( 2 ) INFORMATION FOR SEQ ID NO:66:

( i ) SEQUENCE CHARACTERISTICS:
( A ) LENGTH: 116 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:66:

AGATTCCCTA GTCGATGCCC CGTAGATCAG CAGCTTTGGA GCCTTACCGG GTTTCTGCTG            60
ATACCAGGCC AAGTAGTTCT TTTGATTTCC ACTGTTTAAC AGACTCTGAG AGCTCT              116

( 2 ) INFORMATION FOR SEQ ID NO:67:

( i ) SEQUENCE CHARACTERISTICS:
( A ) LENGTH: 116 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:67:

TCTACGGGGC ATCGACTAGG GAATCTGGGG TACCAGATAG ATTCAGCGGT AGCGGTAGCG            60
GAACCGACTT CACCTTCACC ATCAGCAGCC TGCAGCCAGA GGACATCGCC ACCTAC              116

( 2 ) INFORMATION FOR SEQ ID NO:68:

( i ) SEQUENCE CHARACTERISTICS:
 ( A ) LENGTH: 117 base pairs
 ( B ) TYPE: nucleic acid
 ( C ) STRANDEDNESS: single
 ( D ) TOPOLOGY: linear ( i i ) MOLECULE TYPE: DNA (genomic)

( x i ) SEQUENCE DESCRIPTION: SEQ ID NO:68:

```
TCGATGCCAA GCTTGGCGCC GCCACAGTAC GTTGATCTC CACCTTGGTC CCTTGTCCGA      60
ACGTGAATGG AAAACTATGA ACATTCTGGC AGTAGTAGGT GGCGATGTCC TCTGGCT        117
```

( 2 ) INFORMATION FOR SEQ ID NO:69:

( i ) SEQUENCE CHARACTERISTICS:
 ( A ) LENGTH: 339 base pairs
 ( B ) TYPE: nucleic acid
 ( C ) STRANDEDNESS: double
 ( D ) TOPOLOGY: linear ( i i ) MOLECULE TYPE: DNA (genomic)

( x i ) SEQUENCE DESCRIPTION: SEQ ID NO:69:

```
GATATCGTGA TGACCCAGAG CCCAAGCAGC CTGAGCGCTA GCGTGGGTGA CAGAGTGACC      60
ATCACCTGTA AGAGCTCTCA GAGTCTGTTA AACAGTGGAA ATCAAAAGAA CTACTTGGCC     120
TGGTATCAGC AGAAACCCGG TAAGGCTCCA AAGCTGCTGA TCTACGGGGC ATCGACTAGG     180
GAATCTGGGG TACCAGATAG ATTCAGCGGT AGCGGTAGCG GAACCGACTT CACCTTCACC     240
ATCAGCAGCC TGCAGCCAGA GGACATCGCC ACCTACTACT GCCAGAATGT TCATAGTTTT     300
CCATTCACGT TCGGACAAGG GACCAAGGTG GAGATCAAA                           339
```

( 2 ) INFORMATION FOR SEQ ID NO:70:

( i ) SEQUENCE CHARACTERISTICS:
 ( A ) LENGTH: 113 amino acids
 ( B ) TYPE: amino acid
 ( C ) STRANDEDNESS: single
 ( D ) TOPOLOGY: linear ( i i ) MOLECULE TYPE: protein ( x i ) SEQUENCE DESCRIPTION: SEQ ID NO:70:

```
Asp Ile Val Met Thr Gln Ser Pro Ser Ser Leu Ser Ala Ser Val Gly
 1               5                  10                  15
Asp Arg Val Thr Ile Thr Cys Lys Ser Ser Gln Ser Leu Leu Asn Ser
                20                  25                  30
Gly Asn Gln Lys Asn Tyr Leu Ala Trp Tyr Gln Gln Lys Pro Gly Lys
            35                  40                  45
Ala Pro Lys Leu Leu Ile Tyr Gly Ala Ser Thr Arg Glu Ser Gly Val
        50                  55                  60
Pro Asp Arg Phe Ser Gly Ser Gly Ser Gly Thr Asp Phe Thr Phe Thr
65                  70                  75                  80
Ile Ser Ser Leu Gln Pro Glu Asp Ile Ala Thr Tyr Tyr Cys Gln Asn
                85                  90                  95
Val His Ser Phe Pro Phe Thr Phe Gly Gln Gly Thr Lys Val Glu Ile
            100                 105                 110
Lys
```

( 2 ) INFORMATION FOR SEQ ID NO:71:

( i ) SEQUENCE CHARACTERISTICS:

-continued (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:71:

GATTACGAAT TCGTAGTCGG ATAT                                    24

(2) INFORMATION FOR SEQ ID NO:72:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:72:

TGCCAAGCTT GGCGCCGCCA CAGT                                    24

(2) INFORMATION FOR SEQ ID NO:73:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:73:

CTAGTGCGGG TGACCGAGTG ACCATCACCT GTAAGAGCT                    39

(2) INFORMATION FOR SEQ ID NO:74:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:74:

CTTACAGGTG ATGGTCACTC GGTCACCCGC A                            31

(2) INFORMATION FOR SEQ ID NO:75:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:75:

GGTCTATTAC TGTGCTCGGG ATCCCCTTC TTCCTTACTA CGGCTTGACT ACTGGGGACA    60

AGGTAC                                                             66

(2) INFORMATION FOR SEQ ID NO:76:

(i) SEQUENCE CHARACTERISTICS:
        (A) LENGTH: 64 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:76:

```
CTTGTCCCA GTAGTCAAGC CGTAGTAAGG AAGAAGGGGG ATCCCGAGCA CAGTAATAGA        60
CCGC                                                                    64
```

METHOD FOR TREATMENT AND DIAGNOSIS OF IL-5 MEDIATED DISORDERS

CROSS REFERENCE TO RELATED APPLICATIONS

This application is a continuation-in-part of PCT/US95/17082 filed Dec. 22, 1995, which is a continuation-in-part of U.S. Ser. Nos. 08/470,110 and 08/467,420, both filed Jun. 6, 1995, now U.S. Pat. No. 5,693,323 and U.S. Pat. No. 5,683,892, respectively, which are continuation-in-parts of U.S. Ser. No. 08/363,131 filed Dec. 23, 1994.

FIELD OF THE INVENTION

The present invention relates generally to treatment and diagnosis of conditions mediated by IL-5 and excess eosinophil production, and more specifically to mAbs and other altered antibodies such as Fabs, chimeric, human and humanized antibodies.

BACKGROUND OF THE INVENTION

Eosinophils have been implicated in the pathogenesis of a wide variety of inflammatory disease states including allergic disorders associated with hypersensitivity reactions in the lung tissue (Butterfield et al., In: *Immunopharmacology of Eosinophils*, H. Smith and R. Cook, Eds., p.151–192, Academic Press, London (1993)). A notable example is asthma, a disease characterized by reversible obstruction of the airways leading to non-specific bronchial hyperresponsiveness. This in turn is dependent upon the generation of a chronic inflammatory reaction at the level of the bronchial mucosa and a characteristic infiltration by macrophages, lymphocytes and eosinophils. The eosinophil appears to play a central role in initiating the mucosal damage typical of the disease (Corrigan et al., *Immunol. Today*, 13:501–507 (1992)). Increased numbers of activated eosinophils have been reported in the circulation, bronchial secretions and lung parenchyma of patients with chronic asthma, and the severity of the disease, as measured by a variety of lung function tests, correlates with blood eosinophil numbers (Griffen et al., *J. Aller. Clin. Immunol.*, 67:548–557 (1991)). Increased numbers of eosinophils, often in the process of degranulation, have also been recovered in bronchoalveolar lavage (BAL) fluids of patients undergoing late asthmatic reactions, and reducing eosinophil numbers, usually as a consequence of steroid therapy, is associated with improvements in clinical symptoms (Bousquet et al., *N. Eng. J. Med.*, 323:1033–1039 (1990)).

Interleukin 5 (IL-5) is a homodimeric glycoprotein produced predominantly by activated CD4+ T lymphocytes. In man, IL-5 is largely responsible for controlling the growth and differentiation of eosinophils. Elevated levels of IL-5 are detected in the bronchoalveolar lavage washings of asthmatics (Motojima et al., *Allergy*, 48:98 (1993)). Mice which are transgenic for IL-5 show a marked eosinophilia in peripheral blood and tissues in the absence of antigenic stimulation (Dent et al., *J. Exp. Med.*, 172:1425 (1990)) and anti-murine IL-5 monoclonal antibodies have been shown to have an effect in reducing eosinophilia in the blood and tissues of mice (Hitoshi et al., *Int. Immunol.*, 3:135 (1991)) as well as the eosinophilia associated with parasite infection and allergen challenge in experimental animals (Coffman et al., *Science*, 245:308–310 (1989), Sher et al., *Proc. Natl. Acad. Sci.*, 83:61–65 (1990), Chand et al., *Eur. J. Pharmacol.*, 211:121–123 (1992)).

Although corticosteroids are extremely effective in suppressing eosinophil numbers and other inflammatory components of asthma, there are concerns about their side effects in both severe asthmatics and more recently in mild to moderate asthmatics. The only other major anti-inflammatory drug therapies—cromoglycates (cromolyn sodium and nedocromil)—are considerably less effective than corticosteroids and their precise mechanism of action remains unknown.

More recent developments have focused on new inhaled steroids, longer acting bronchodilators and agents acting on novel biochemical or pharmacological targets (e.g., potassium channel activators, leukotriene antagonists, 5-lipoxygenase (5-LO) inhibitors etc.). An ideal drug would be one that combines the efficacy of steroids with the safety associated with cromolyn sodium, yet has increased selectivity and more rapid onset of action. Neutralizing IL-5 antibodies may potentially be useful in relieving eosinophila-related symptoms in man.

Hence there is a need in the art for a high affinity IL-5 antagonist, such as a neutralizing monoclonal antibody to human interleukin 5, which would reduce eosinophil differentiation and proliferation (i.e., accumulation of eosinophils) and thus eosinophil inflammation.

SUMMARY OF THE INVENTION

In a first aspect, the present invention provides an improved method for treating conditions associated with excess eosinophil production wherein the improvement comprises the step of administering a neutralizing monoclonal antibody for human IL-5, which does not block binding of human IL-5 to the human IL-5 receptor α-chain. Exemplary of such monoclonal antibodies is rat monoclonal antibody 4A6.

In yet another aspect of the invention is a method to assess the presence or absence of a human IL-5 soluble receptor (α-chain/human IL-5 complex in a human which comprises obtaining a sample of biological fluid from a patient and allowing a monoclonal antibody for human IL-5 which does not block binding of human IL-5 to the α-chain of the human IL-5 receptor to come in contact with such sample under conditions such that a human IL-5 soluble receptor α-chain/human IL-5/monoclonal antibody complex can form and detecting the presence or absence of said human IL-5 soluble receptor α-chain/human IL-5/ monoclonal antibody complex. This method can be used to diagnose conditions associated with excess eosinophil production in a human and also to track progress and treatment of such disorders.

In a further aspect, the present invention provides a method of screening compounds to identify those compounds which antagonize binding of IL-5, IL-5/IL-5 receptor α-chain complex, or IL-5/IL-5 receptor α-chain/mAb complex to a human IL-5 receptor β-chain which comprises contacting the human IL-5 receptor β-chain with a plurality of candidate compounds under conditions to permit binding to the IL-5 receptor β-chain and identifying those candidate compounds that antagonize binding of said IL-5, IL-5/IL-5 receptor α-chain complex, or IL-5/IL-5 receptor α-chain/ mAb complex to the IL-5 receptor β-chain.

Other aspects and advantages of the present invention are described further in the detailed description and the preferred embodiments thereof.

BRIEF DESCRIPTION OF THE DRAWINGS

FIG. 1 [SEQ ID NOS: 1 and 15] illustrates the heavy chain variable region for the murine antibody 2B6, and the murine/human 2B6 chimeric antibody. The boxed areas indicate the CDRs.

FIG. 2 [SEQ ID NOS: 2 and 16] illustrates the light chain variable region for the murine antibody 2B6, and the murine/human 2B6 chimeric antibody. The boxed areas indicate the CDRs.

FIG. 3 [SEQ ID NO:3] illustrates the heavy chain variable region for the murine antibody 2F2. The boxed areas indicate the CDRs.

FIG. 4 [SEQ ID NO:4] illustrates the light chain variable region for the murine antibody 2F2. The boxed areas indicate the CDRs.

FIG. 5 [SEQ ID NO:5] illustrates the heavy chain variable region for the murine antibody 2E3. The boxed areas indicate the CDRs.

FIG. 6 [SEQ ID NO:6] illustrates the light chain variable region for the murine antibody 2E3. The boxed areas indicate the CDRs.

FIG. 7 [SEQ ID NOs:7–14] illustrates the heavy and light chain CDRs from murine antibodies 2B6, 2F2 and 2E3.

FIG. 8 [SEQ ID NOS: 18, 19] illustrates the heavy chain variable region for the humanized antibody 2B6. The boxed areas indicate the CDRs.

FIG. 9 [SEQ ID NOs: 20, 21] illustrates the light chain variable region for the humanized antibody 2B6. The boxed areas indicate the CDRs.

FIG: 10 is a schematic drawing of plasmid pCDIL5HZHC1.0 employed to express a humanized heavy chain gene in mammalian cells. The plasmid contains a beta lactamase gene (BETA LAC), an SV-40 origin of replication (SV40), a cytomegalovirus promoter sequence (CMV), a signal sequence, the humanized heavy chain, a poly A signal from bovine growth hormone (BGH), a betaglobin promoter (beta glopro), a dihydrofolate reductase gene (DHFR), and another BGH sequence poly A signal in a pUC19 background.

Figure 11:
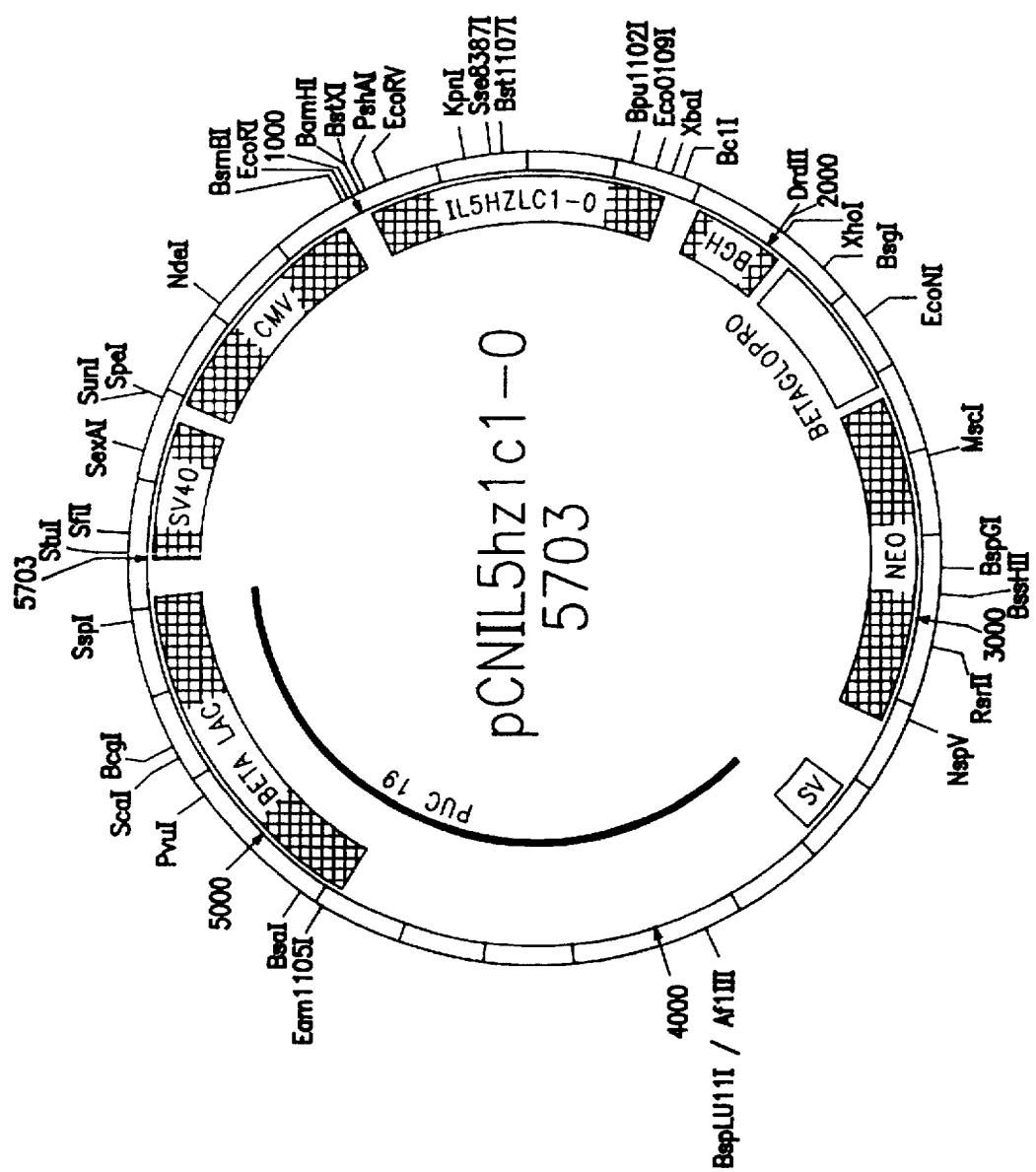

FIG. 11 is a schematic drawing of plasmid pCNIL5HZLC1.0 employed to express a humanized light chain gene in mammalian cells.

FIG. 12 [SEQ ID NOs: 61, 62] illustrates the NewM heavy chain variable region for the humanized antibody 2B6. The boxed areas indicate the CDRs.

FIG. 13 [SEQ ID NOs: 69, 70] illustrates the REI light chain variable region for the humanized antibody 2B6. The boxed areas indicate the CDRs.

DETAILED DESCRIPTION OF THE INVENTION

The present invention provides a variety of antibodies, altered antibodies and fragments thereof, which are characterized by human IL-5 binding specificity, neutralizing activity, and high affinity for human IL-5 as exemplified in murine monoclonal antibody 2B6 or rat antibody 4A6. The antibodies of the present invention were prepared by conventional hybridoma techniques, phage display combinatorial libraries, immunoglobulin chain shuffling, and humanization techniques to generate novel neutralizing antibodies. These products are useful in therapeutic and pharmaceutical compositions for treating IL-5-mediated disorders, e.g., asthma. These products are also useful in the diagnosis of IL-5-mediated conditions by measurement (e.g., enzyme linked immunosorbent assay (ELISA)) of endogenous IL-5 levels in humans or IL-5 released ex vivo from activated cells.

Preferably the antibodies of the invention bind to human IL-5, but do not block the interaction between human IL-5 and IL-5 receptor α-chain. That is, the preferred antibodies are non-competitive with the IL-5 receptor α-chain for human IL-5. The preferred antibodies of the invention also bind to an IL-5/IL-5 receptor α-chain complex. A naturally-occurring soluble form of the IL-5 receptor α-chain has been observed in vitro (see, e.g., Tavernier et al., *Cell*, 66:1175–1184 (1991)) but it was not known, prior to the this invention, whether a soluble form of the IL-5 receptor α-chain was produced in vivo. Applicants have identified a soluble form of the IL-5 receptor α-chain in vivo. Thus, an antibody that binds to complexed IL-5/IL-5 receptor α-chain would be a more effective therapeutic for it would bind "free" or uncomplexed IL-5 as well as complexed IL-5. In addition, the soluble form of the IL-5 receptor α-chain may be a natural antagonist of human IL-5. Hence, an antibody that does not compete with the soluble receptor is a more desirable and effective antagonist of IL-5, and thus it is an improved therapeutic (relative to mAbs that do compete with the IL-5 receptor α-chain for binding to IL-5) for treating IL-5 mediated conditions such as excess eosinophil production.

I. Definitions. "Altered antibody" refers to a protein encoded by an altered immunoglobulin coding region, which may be obtained by expression in a selected host cell. Such altered antibodies are engineered antibodies (e.g., chimeric or humanized antibodies) or antibody fragments lacking all or part of an immunoglobulin constant region, e.g., Fv, Fab, or F(ab)$_2$ and the like. "Altered immunoglobulin coding region" refers to a nucleic acid sequence encoding altered antibody of the invention. When the altered antibody is a CDR-grafted or humanized antibody, the sequences that encode the complementarity determining regions (CDRs) from a non-human immunoglobulin are inserted into a first immunoglobulin partner comprising human variable framework sequences. Optionally, the first immunoglobulin partner is operatively linked to a second immunoglobulin partner. "First immunoglobulin partner" refers to a nucleic acid sequence encoding a human framework or human immunoglobulin variable region in which the native (or naturally-occurring) CDR-encoding regions are replaced by the CDR-encoding regions of a donor antibody. The human variable region can be an immunoglobulin heavy chain, a light chain (or both chains), an analog or functional fragments thereof. Such CDR regions, located within the variable region of antibodies (immunoglobulins) can be determined by known methods in the art. For example Kabat et al. (*Sequences of Proteins of Immunological Interest*, 4th Ed., U.S. Department of Health and Human Services, National Institutes of Health (1987)) disclose rules for locating CDRs. In addition, computer programs are known which are useful for identifying CDR regions/structures. "Neutralizing" refers to an antibody that inhibits IL-5 activity by preventing the binding of human IL-5 to its specific receptor or by inhibiting the signaling of IL-5 through its receptor, should binding occur. A mAb is neutralizing if it is 90% effective, preferably 95% effective and most preferably 100% effective in inhibiting IL-5 activity as measured in the B 13 cell bioassay (IL-5 Neutralization assay, see Example 2C).

The term "high affinity" refers to an antibody having a binding affinity characterized by a $K_d$ equal to or less than $3.5 \times 10^{-11}$M for human IL-5 as determined by optical biosensor anaylsis (see Example 2D).

By "binding specificity for human IL-5" is meant a high affinity for human, not murine, IL-5.

"Second immunoglobulin partner" refers to another nucleotide sequence encoding a protein or peptide to which the first immunoglobulin partner is fused in frame or by means of an optional conventional linker sequence (i.e., operatively linked). Preferably it is an immunoglobulin gene. The second immunoglobulin partner may include a nucleic acid sequence encoding the entire constant region for the same (i.e., homologous - the first and second altered antibodies are derived from the same source) or an additional (i.e., heterologous) antibody of interest. It may be an immunoglobulin heavy chain or light chain (or both chains as part of a single polypeptide). The second immunoglobulin partner is not limited to a particular immunoglobulin class or isotype. In addition, the second immunoglobulin partner may comprise part of an immunoglobulin constant region, such as found in a Fab, or F(ab)$_2$ (i.e., a discrete part of an appropriate human constant region or framework region). Such second immunoglobulin partner may also comprise a sequence encoding an integral membrane protein exposed on the outer surface of a host cell, e.g., as part of a phage display library, or a sequence encoding a protein for analytical or diagnostic detection, e.g., horseradish peroxidase, β-galactosidase, etc.

The terms Fv, Fc, Fd, Fab, or F(ab)$_2$ are used with their standard meanings (see, e.g., Harlow et al., *Antibodies A Laboratory Manual*, Cold Spring Harbor Laboratory, (1988)).

As used herein, an "engineered antibody" describes a type of altered antibody, i.e., a full-length synthetic antibody (e.g., a chimeric or humanized antibody as opposed to an antibody fragment) in which a portion of the light and/or heavy chain variable domains of a selected acceptor antibody are replaced by analogous parts from one or more donor antibodies which have specificity for the selected epitope. For example, such molecules may include antibodies characterized by a humanized heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one or more CDRs (preferably all) from the acceptor antibody with CDRs from a donor antibody described herein.

A "chimeric antibody" refers to a type of engineered antibody which contains naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., *Proc. Natl Acad Sci USA*, 86:10029–10032 (1989), Hodgson et al., *Bio/Technology*, 9:421 (1991)).

The term "donor antibody" refers to an antibody (monoclonal, or recombinant) which contributes the nucleic acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody. One donor antibody suitable for use in this invention is a non-human neutralizing monoclonal antibody (i.e., murine) designated as 2B6. The antibody 2B6 is defined as a high affinity, human-IL-5 specific (i.e., does not recognize murine IL-5), neutralizing antibody of isotype IgG$_1$ having the variable light chain DNA and amino acid sequences of SEQ ID NOs: 2 and 16, respectively, and the variable heavy chain DNA and amino acid sequences of SEQ ID NOs: 1 and 15, respectively, on a suitable murine IgG constant region.

The term "acceptor antibody" refers to an antibody (monoclonal; or recombinant) heterologous to the donor antibody, which contributes all (or any portion, but preferably all) of the nucleic acid sequences encoding its heavy and/or light chain framework regions and/or its heavy and/or light chain constant regions to the first immunoglobulin partner. Preferably a human antibody is the acceptor antibody.

"CDRs" are defined as the complementarity determining region amino acid sequences of an antibody which are the hypervariable regions of immunoglobulin heavy and light chains. See, e.g., Kabat et al., *Sequences of Proteins of Immunological Interest*, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate).

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

By 'sharing the antigen binding specificity or neutralizing ability' is meant, for example, that although mAb 2B6 may be characterized by a certain level of antigen affinity, a CDR encoded by a nucleic acid sequence of 2B6 in an appropriate structural environment may have a lower, or higher affinity. It is expected that CDRs of 2B6 in such environments will nevertheless recognize the same epitope(s) as 2B6. Exemplary heavy chain CDRs of 2B6 include SEQ ID NO: 7; SEQ ID NO: 8; SEQ ID NO: 9; and exemplary light chain CDRs of 2B6 include SEQ ID NO: 10; SEQ ID NO: 11; and SEQ ID NO: 12.

A "functional fragment" is a partial heavy or light chain variable sequence (e.g., minor deletions at the amino or carboxy terminus of the immunoglobulin variable region) which retains the same antigen binding specificity and/or neutralizing ability as the antibody from which the fragment was derived.

An "analog" is an amino acid sequence modified by at least one amino acid, wherein said modification can be chemical or a substitution or a rearrangement of a few amino acids (i.e., no more than 10), which modification permits the amino acid sequence to retain the biological characteristics, e.g., antigen specificity and high affinity, of the unmodified sequence. For example, (silent) mutations can be constructed, via substitutions, when certain endonuclease restriction sites are created within or surrounding CDR-encoding regions.

Analogs may also arise as allelic variations. An "allelic variation or modification" is an alteration in the nucleic acid sequence encoding the amino acid or peptide sequences of the invention. Such variations or modifications may be due to degeneracy in the genetic code or may be deliberately engineered to provide desired characteristics. These variations or modifications may or may not result in alterations in any encoded amino acid sequence.

The term "effector agents" refers to non-protein carrier molecules to which the altered antibodies, and/or natural or synthetic light or heavy chains of the donor antibody or other fragments of the donor antibody may be associated by conventional means. Such non-protein carriers can include conventional carriers used in the diagnostic field, e.g., polystyrene or other plastic beads, polysaccharides, e.g., as used in the BIAcore [Pharmacia] system, or other non-protein substances useful in the medical field and safe for administration to humans and animals. Other effector agents may include a macrocycle, for chelating a heavy metal atom, or radioisotopes. Such effector agents may also be useful to increase the half-life of the altered antibodies, e.g., polyethylene glycol..

"Conditions associated with excess eosinophil production" refer to allergic and/or atopic responses, or to responses associated with eosinophilia, such as but not limited to, allergic rhinitis and asthma.

II. High Affinity IL-5 Monoclonal Antibodies

For use in constructing the antibodies, altered antibodies and fragments of this invention, a non-human species (for example, bovine, ovine, monkey, chicken, rodent (e.g., murine and rat), etc.) may be employed to generate a desirable immunoglobulin upon presentment with native human IL-5 or a peptide epitope therefrom. Conventional hybridoma techniques are employed to provide a hybridoma cell line secreting a non-human mAb to IL-5. Such hybridomas are then screened for binding using IL-5 coated to 96-well plates, as described in the Examples section, or alternatively with biotinylated IL-5 bound to a streptavidin coated plate.

One exemplary, high affinity, neutralizing mAb of this instant invention is mAb 2B6, a murine antibody which can be used for the development of a chimeric or humanized antibody, described in more detail in Example 1 below. The 2B6 mAb is characterized by an antigen binding specificity for human IL-5, with a $K_d$ of less than $3.5 \times 10^{-11}$M (about $2.2 \times 10^{-11}$M) for IL-5. The $K_d$ for IL-5 of a Fab fragment from 2B6 (see, Example 3H) is estimated to be about $9 \times 10^{-11}$M as determined by optical biosensor. MAb 2B6 appears to block the binding interaction between human IL-5 and the a-chain of the human IL-5 receptor.

Another desirable donor antibody is the murine mAb, 2E3. This mAb is characterized by being isotype IgG$_{2a}$, and having a dissociation constant for hIL-5 of less than $3.5 \times 10^{-11}$M (about $2.0 \times 10^{-11}$M).

Yet, another desirable donor antibody is the rat mAb, 4A6. This mAb is characterized by having a dissociation constant for hIL-5 of less than $3.5 \times 10^{-11}$M (about $1.8 \times 10^{-11}$M). In addition, mAb 4A6 appears to block the binding interaction between human IL-5 and the β-chain of the IL-5 receptor. MAb 4A6 does not block binding of human IL-5 to the α-chain of the IL-5 receptor. Thus, mAb 4A6 binds human IL-5 and an IL-5/IL-5 receptor α-chain complex.

This invention is not limited to the use of the 2B6 mAb, the 2E3 mAb, or its hypervariable (i.e., CDR) sequences. Any other appropriate high affinity IL-5 antibodies characterized by a dissociation constant equal or less than $3.5 \times 10^{-11}$M for human IL-5 and corresponding anti-IL-5 CDRs may be substituted therefor. Wherever in the following description the donor antibody is identified as 2B6 or 2E3, this designation is made for illustration and simplicity of description only.

III. Antibody Fragments

The present invention also includes the use of Fab fragments or F(ab')$_2$ fragments derived from mAbs directed against human IL-5. These fragments are useful as agents protective in vivo against IL-5 and eosinophil-mediated conditions or in vitro as part of an IL-5 diagnostic. A Fab fragment contains the entire light chain and amino terminal portion of the heavy chain; and an F(ab')$_2$ fragment is the fragment formed by two Fab fragments bound by disulfide bonds. MAbs 2B6, 2E3, and other similar high affinity, IL-5 binding antibodies, provide sources of Fab fragments and F(ab')$_2$ fragments which can be obtained by conventional means, e.g., cleavage of the mAb with the appropriate proteolytic enzymes, papain and/or pepsin, or by recombinant methods. These Fab and F(ab')$_2$ fragments are useful themselves as therapeutic, prophylactic or diagnostic agents, and as donors of sequences including the variable regions and CDR sequences useful in the formation of recombinant or humanized antibodies as described herein.

The Fab and F(ab')$_2$ fragments can be constructed via a combinatorial phage library (see, e.g., Winter et al., *Ann. Rev. Immunol.*, 12:433–455 (1994)) or via immunoglobulin chain shuffling (see, e.g., Marks et al., *Bio/Technology*, 10:779–783 (1992), which are both hereby incorporated by reference in their entirety) wherein the Fd or $v_H$ immunoglobulin from a selected antibody (e.g., 2B6) is allowed to associate with a repertoire of light chain immunoglobulins, $v_L$ (or $v_K$), to form novel Fabs. Conversely, the light chain immunoglobulin from a selected antibody may be allowed to associate with a repertoire of heavy chain immunoglobulins, $v_H$ (or Fd), to form novel Fabs. Neutralizing IL-5 Fabs were obtained when the Fd of mAb 2B6 was allowed to associate with a repertoire of light chain immunoglobulins, as described in more detail in the Examples section. Hence, one is able to recover neutralizing Fabs with unique sequences (nucleotide and amino acid) from the chain shuffling technique.

IV. Anti-IL-5 Amino Acid and Nucleotide Sequences of Interest

The mAb 2B6 or other antibodies described above may contribute sequences, such as variable heavy and/or light chain peptide sequences, framework sequences, CDR sequences, functional fragments, and analogs thereof, and the nucleic acid sequences encoding them, useful in designing and obtaining various altered antibodies which are characterized by the antigen binding specificity of the donor antibody.

As one example, the present invention thus provides variable light chain and variable heavy chain sequences from the IL-5 murine antibody 2B6 and sequences derived therefrom. The heavy chain variable region of 2B6 is illustrated by FIG. 1. The CDR-encoding regions are indicated by the boxed areas and are provided in SEQ ID NO: 7; SEQ ID NO: 8; and SEQ ID NO: 9. The light chain clone variable region of 2B6 is illustrated by FIG. 2. The CDR-encoding regions are provided in SEQ ID NO: 10; SEQ ID NO: 11; and SEQ ID NO: 12.

A humanized heavy chain variable region is illustrated in FIG. 8 [SEQ ID NOs: 18 and 19]. The signal sequence is also provided in SEQ ID NO: 17. Other suitable signal sequences, known to those of skill in the art, may be substituted for the signal sequences exemplified herein. The CDR amino acid sequences of this construct are identical to the native murine and chimeric heavy chain CDRs and are provided by SEQ ID NO: 7, SEQ ID NO: 8, and SEQ ID NO: 9. An exemplary (synthetic) humanized light chain variable sequence is illustrated in FIG. 9 [SEQ ID NOs: 20 and 21].

The nucleic acid sequences of this invention, or fragments thereof, encoding the variable light chain and heavy chain peptide sequences are also useful for mutagenic introduction of specific changes within the nucleic acid sequences encoding the CDRs or framework regions, and for incorporation of the resulting modified or fusion nucleic acid sequence into a plasmid for expression. For example, silent substitutions in the nucleotide sequence of the framework and CDR-encoding regions were used to create restriction enzyme sites which facilitated insertion of mutagenized CDR (and/or framework) regions. These CDR-encoding regions were used in the construction of a humanized antibody of this invention.

Taking into account the degeneracy of the genetic code, various coding sequences may be constructed which encode the variable heavy and light chain amino acid sequences, and CDR sequences of the invention as well as functional fragments and analogs thereof which share the antigen specificity of the donor antibody. The isolated nucleic acid sequences of this invention, or fragments thereof, encoding the variable chain peptide sequences or CDRs can be used to produce altered antibodies, e.g., chimeric or humanized antibodies, or other engineered antibodies of this invention when operatively combined with a second immunoglobulin partner.

It should be noted that in addition to isolated nucleic acid sequences encoding portions of the altered antibody and antibodies described herein, other such nucleic acid sequences are encompassed by the present invention, such as those complementary to the native CDR-encoding sequences or complementary to the modified human framework regions surrounding the CDR-encoding regions. Useful DNA sequences include those sequences which hybridize under stringent hybridization conditions [see, T. Maniatis et al, *Molecular Cloning (A Laboratory Manual)*, Cold Spring Harbor Laboratory (1982), pages 387 to 389] to the DNA sequences. An example of one such stringent hybridization condition is hybridization at 4XSSC at 650 C, followed by a washing in 0.1XSSC at 65° C. for an hour. Alternatively an exemplary stringent hybridization condition is in 50% formamide, 4XSSC at 42° C. Preferably, these hybridizing DNA sequences are at least about 18 nucleotides in length, i.e., about the size of a CDR.

V. Altered immunoglobulin molecules and Altered antibodies

Altered immunoglobulin molecules can encode altered antibodies which include engineered antibodies such as chimeric antibodies and humanized antibodies. A desired altered immunoglobulin coding region contains CDR-encoding regions that encode peptides having the antigen specificity of an IL-5 antibody, preferably a high affinity antibody such as provided by the present invention, inserted into a first immunoglobulin partner (a human framework or human immunoglobulin variable region).

Preferably, the first immunoglobulin partner is operatively linked to a second immunoglobulin partner. The second immunoglobulin partner is defined above, and may include a sequence encoding a second antibody region of interest, for example an Fc region. Second immunoglobulin partners may also include sequences encoding another immunoglobulin to which the light or heavy chain constant region is fused in frame or by means of a linker sequence. Engineered antibodies directed against functional fragments or analogs of IL-5 may be designed to elicit enhanced binding with the same antibody.

The second immunoglobulin partner may also be associated with effector agents as defined above, including non-protein carrier molecules, to which the second immunoglobulin partner may be operatively linked by conventional means.

Fusion or linkage between the second immunoglobulin partners, e.g., antibody sequences, and the effector agent may be by any suitable means, e.g., by conventional covalent or ionic bonds, protein fusions, or hetero-bifunctional cross-linkers, e.g., carbodiinide, glutaraldehyde, and the like. Such techniques are known in the art and readily described in conventional chemistry and biochemistry texts.

Additionally, conventional linker sequences which simply provide for a desired amount of space between the second immunoglobulin partner and the effector agent may also be constructed into the altered immunoglobulin coding region. The design of such linkers is well known to those of skill in the art.

In addition, signal sequences for the molecules of the invention may be modified to enhance expression. As one example the 2B6 humanized antibody having the signal sequence and CDRs derived from the murine heavy chain sequence, had the original signal peptide replaced with another signal sequence [SEQ ID NO: 17].

An exemplary altered antibody contains a variable heavy and/or light chain peptide or protein sequence having the antigen specificity of mAb 2B6, e.g., the $V_H$ and $V_L$ chains. Still another desirable altered antibody of this invention is characterized by the amino acid sequence containing at least one, and preferably all of the CDRs of the variable region of the heavy and/or light chains of the murine antibody molecule 2B6 with the remaining sequences being derived from a human source, or a functional fragment or analog thereof. See, e.g., the humanized $V_H$ and $V_L$ regions (FIGS. 8 and 9).

In still a further embodiment, the engineered antibody of the invention may have attached to it an additional agent. For example, the procedure of recombinant DNA technology may be used to produce an engineered antibody of the invention in which the Fc fragment or CH2 CH3 domain of a complete antibody molecule has been replaced by an enzyme or other detectable molecule (i.e., a polypeptide effector or reporter molecule).

The second immunoglobulin partner may also be operatively linked to a non-immunoglobulin peptide, protein or fragment thereof heterologous to the CDR-containing sequence having the antigen specificity of murine 2B6. The resulting protein may exhibit both anti-IL-5 antigen specificity and characteristics of the non-immunoglobulin upon expression. That fusion partner characteristic may be, e.g., a functional characteristic such as another binding or receptor domain, or a therapeutic characteristic if the fusion partner is itself a therapeutic protein, or additional antigenic characteristics.

Another desirable protein of this invention may comprise a complete antibody molecule, having full length heavy and light chains, or any discrete fragment thereof, such as the Fab or F(ab')$_2$ fragments, a heavy chain dimer, or any minimal recombinant fragments thereof such as an $F_v$, or a single-chain antibody (SCA) or any other molecule with the same specificity as the selected donor mAb, e.g., mAb 2B6 or 2E3. Such protein may be used in the form of an altered antibody, or may be used in its unfused form.

Whenever the second immunoglobulin partner is derived from an antibody different from the donor antibody, e.g., any isotype or class of immunoglobulin framework or constant regions, an engineered antibody results. Engineered antibodies can comprise immunoglobulin (Ig) constant regions and variable framework regions from one source, e.g., the acceptor antibody, and one or more (preferably all) CDRs from the donor antibody, e.g., the anti-IL-5 antibody described herein. In addition, alterations, e.g., deletions, substitutions, or additions, of the acceptor mAb light and/or heavy variable domain framework region at the nucleic acid or amino acid levels, or the donor CDR regions may be made in order to retain donor antibody antigen binding specificity.

Such engineered antibodies are designed to employ one (or both) of the variable heavy and/or light chains of the IL-5 mAb (optionally modified as described) or one or more of the below-identified heavy or light chain CDRs (see also FIG. 7). The engineered antibodies of the invention are neutralizing, i.e., they desirably block binding to the receptor of the IL-5 protein and they also block or prevent proliferation of IL-5 dependent cells.

Such engineered antibodies may include a humanized antibody containing the framework regions of a selected human immunoglobulin or subtype., or a chimeric antibody containing the human heavy and light chain constant regions fused to the IL-5 antibody functional fragments. A suitable human (or other animal) acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody.

Desirably the heterologous framework and constant regions are selected from human immunoglobulin classes and isotypes, such as IgG (subtypes 1 through 4), IgM, IgA, and IgE. However, the acceptor antibody need not comprise only human immunoglobulin protein sequences. For instance a gene may be constructed in which a DNA sequence encoding part of a human immunoglobulin chain is fused to a DNA sequence encoding a non-immunoglobulin amino acid sequence such as a polypeptide effector or reporter molecule.

One example of a particularly desirable humanized antibody contains CDRs of 2B6 inserted onto the framework regions of a selected human antibody sequence. For neutralizing humanized antibodies, one, two or preferably three CDRs from the IL-5 antibody heavy chain and/or light chain variable regions are inserted into the framework regions of the selected human antibody sequence, replacing the native CDRs of the latter antibody.

Preferably, in a humanized antibody, the variable domains in both human heavy and light chains have been engineered by one or more CDR replacements. It is possible to use all six CDRs, or various combinations of less than the six CDRs. Preferably all six CDRs are replaced. It is possible to replace the CDRs only in the human heavy chain, using as light chain the unmodified light chain from the human acceptor antibody. Still alternatively, a compatible light chain may be selected from another human antibody by recourse to the conventional antibody databases. The remainder of the engineered antibody may be derived from any suitable acceptor human immunoglobulin.

The engineered humanized antibody thus preferably has the structure of a natural human antibody or a fragment thereof, and possesses the combination of properties required for effective therapeutic use, e.g., treatment of IL-5 mediated inflammatory diseases in man, or for diagnostic uses.

As another example, an engineered antibody may contain three CDRs of the variable light chain region of 2E3 [SEQ ID NO: 10, 11 and 13] and three CDRs of the variable heavy chain region of 2B6 [SEQ ID NO: 7, 8 and 9]. The resulting humanized antibody should be characterized by the same antigen binding specificity and high affinity of mAb 2B6.

It will be understood by those skilled in the art that an engineered antibody may be further modified by changes in variable domain amino acids without necessarily affecting the specificity and high affinity of the donor antibody (i.e., an analog). It is anticipated that heavy and light chain amino acids may be substituted by other amino acids either in the variable domain frameworks or CDRs or both.

In addition, the constant region may be altered to enhance or decrease selective properties of the molecules of the instant invention. For example, dimerization, binding to Fc receptors, or the ability to bind and activate complement (see, e.g., Angal et al., *Mol. Immunol*, 30:105–108 (1993), Xu et al., *J. Biol. Chem*, 269:3469–3474 (1994), Winter et al., EP 307,434-B).

An altered antibody which is a chimeric antibody differs from the humanized antibodies described above by providing the entire non-human donor antibody heavy chain and light chain variable regions, including framework regions, in association with human immunoglobulin constant regions for both chains. It is anticipated that chimeric antibodies which retain additional non-human sequence relative to humanized antibodies of this invention may elicit a significant immune response in humans.

Such antibodies are useful in the prevention and treatment of IL-5 mediated disorders, as discussed below.

VI. Production of Altered antibodies and Engineered Antibodies

Preferably, the variable light and/or heavy chain sequences and the CDRs of mAb 2B6 or other suitable donor mAbs (e.g., 2E3, 2F2, 4A6, etc.), and their encoding nucleic acid sequences, are utilized in the construction of altered antibodies, preferably humanized antibodies, of this invention, by the following process. The same or similar techniques may also be employed to generate other embodiments of this invention.

A hybridoma producing a selected donor mAb, e.g., the murine antibody 2B6, is conventionally cloned, and the DNA of its heavy and light chain variable regions obtained by techniques known to one of skill in the art, e.g., the techniques described in Sambrook et al., (*Molecular Cloning (A Laboratory Manual)*, 2nd edition, Cold Spring Harbor Laboratory (1989)). The variable heavy and light regions of 2B6 containing at least the CDR-encoding regions and those portions of the acceptor mAb light and/or heavy variable domain framework regions required in order to retain donor mAb binding specificity, as well as the remaining immunoglobulin-derived parts of the antibody chain derived from a human immunoglobulin are obtained using polynucleotide primers and reverse transcriptase. The CDR-encoding regions are identified using a known database and by comparison to other antibodies.

A mouse/human chimeric antibody may then be prepared and assayed for binding ability. Such a chimeric antibody contains the entire non-human donor antibody $V_H$ and $V_L$ regions, in association with human Ig constant regions for both chains.

Homologous framework regions of a heavy chain variable region from a human antibody were identified using computerized databases, e.g., KABAT®, and a human antibody having homology to 2B6 was selected as the acceptor antibody. The sequences of synthetic heavy chain variable regions containing the 2B6 CDR-encoding regions within the human antibody frameworks were designed with optional nucleotide replacements in the framework regions to incorporate restriction sites. This designed sequence was then synthesized using long synthetic oligomers. Alternatively, the designed sequence can be synthesized by overlapping oligonucleotides, amplified by polymerase chain reaction (PCR), and corrected for errors.

A suitable light chain variable framework region was designed in a similar manner.

A humanized antibody may be derived from the chimeric antibody, or preferably, made synthetically by inserting the donor mAb CDR-encoding regions from the heavy and light chains appropriately within the selected heavy and light chain framework. Alternatively, a humanized antibody of the invention made be prepared using standard mutagenesis techniques. Thus, the resulting humanized antibody contains human framework regions and donor mAb CDR-encoding regions. There may be subsequent manipulation of framework residues. The resulting humanized antibody can be expressed in recombinant host cells, e.g., COS, CHO or myeloma cells. Other humanized antibodies may be prepared using this technique on other suitable IL-5-specific, neutralizing, high affinity, non-human antibodies.

A conventional expression vector or recombinant plasmid is produced by placing these coding sequences for the altered antibody in operative association with conventional regulatory control sequences capable of controlling the replication and expression in, and/or secretion from, a host cell. Regulatory sequences include promoter sequences, e.g., CMV promoter, and signal sequences, which can be derived from other known antibodies. Similarly, a second expression vector can be produced having a DNA sequence which encodes a complementary antibody light or heavy chain. Preferably this second expression vector is identical to the first except insofar as the coding sequences and selectable markers are concerned, so to ensure as far as possible that each polypeptide chain is functionally expressed. Alternatively, the heavy and light chain coding sequences for the altered antibody may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antibody of the invention. The humanized antibody which includes the association of both the recombinant heavy chain and/or light chain is screened from culture by appropriate assay, such as ELISA or RIA. Similar conventional techniques may be employed to construct other altered antibodies and molecules of this invention.

Suitable vectors for the cloning and subcloning steps employed in the methods and construction of the compositions of this invention may be selected by one of skill in the art. For example, the conventional pUC series of cloning vectors, may be used. One vector used is pUC19, which is commercially available from supply houses, such as Amersham (Buckinghamshire, United Kingdom) or Pharmacia (Uppsala, Sweden). Additionally, any vector which is capable of replicating readily, has an abundance of cloning sites and selectable genes (e.g., antibiotic resistance), and is easily manipulated may be used for cloning. Thus, the selection of the cloning vector is not a limiting factor in this invention.

Similarly, the vectors employed for expression of the engineered antibodies according to this invention may be selected by one of skill in the art from any conventional vector. The vectors also contain selected regulatory sequences (such as CMV promoters) which direct the replication and expression of heterologous DNA sequences in selected host cells. These vectors contain the above described DNA sequences which code for the engineered antibody or altered immunoglobulin coding region. In addition, the vectors may incorporate the selected immunoglobulin sequences modified by the insertion of desirable restriction sites for ready manipulation.

The expression vectors may also be characterized by genes suitable for amplifying expression of the heterologous DNA sequences, e.g., the mammalian dihydrofolate reductase gene (DHFR). Other preferable vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell line transfected with a recombinant plasmid containing the coding sequences of the engineered antibodies or altered immunoglobulin molecules thereof. Host cells useful for the cloning and other manipulations of these cloning vectors are also conventional. However, most desirably, cells from various strains of *E. coli* are used for replication of the cloning vectors and other steps in the construction of altered antibodies of this invention.

Suitable host cells or cell lines for the expression of the engineered antibody or altered antibody of the invention are preferably mammalian cells such as CHO, COS, a fibroblast cell (e.g., 3T3), and myeloid cells, and more preferably a CHO or a myeloid cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., cited above.

Bacterial cells may prove useful as host cells suitable for the expression of the recombinant Fabs of the present invention (see, e.g., Plückthun, A., *Immunol. Rev.*, 130:151–188 (1992)). However, due to the tendency of proteins expressed in bacterial cells to be in an unfolded or improperly folded form or in a non-glycosylated form, any recombinant Fab produced in a bacterial cell would have to be screened for retention of antigen binding ability. If the molecule expressed by the bacterial cell was produced in a properly folded form, that bacterial cell would be a desirable host. For example, various strains of *E. coli* used for expression are well-known as host cells in the field of biotechnology. Various strains of *B. subtilis*, Streptomyces, other *bacilli* and the like may also be employed in this method.

Where desired, strains of yeast cells known to those skilled in the art are also available as host cells, as well as insect cells, e.g. Drosophila and Lepidoptera and viral expression systems. See, e.g. Miller et al., *Genetic Engineering*, 8:277–298, Plenum Press (1986) and references cited therein.

The general methods by which the vectors of the invention may be constructed, the transfection methods required to produce the host cells of the invention, and culture methods necessary to produce the altered antibody of the invention from such host cell are all conventional techniques. Likewise, once produced, the altered antibodies of the invention may be purified from the cell culture contents according to standard procedures of the art, including ammonium sulfate precipitation, affinity columns, column chromatography, gel electrophoresis and the like. Such techniques are within the skill of the art and do not limit this invention.

Yet another method of expression of the humanized antibodies may utilize expression in a transgenic animal, such as described in U.S. Pat. No. 4,873,316. This relates to an expression system using the animal's casein promoter which when transgenically incorporated into a mammal permits the female to produce the desired recombinant protein in its milk.

Once expressed by the desired method, the engineered antibody is then examined for in vitro activity by use of an appropriate assay. Presently conventional ELISA assay formats are employed to assess qualitative and quantitative binding of the engineered antibody to IL-5. Additionally, other in vitro assays may also be used to verify neutralizing efficacy prior to subsequent human clinical studies performed to evaluate the persistence of the engineered antibody in the body despite the usual clearance mechanisms.

Following the procedures described for humanized antibodies prepared from 2B6, one of skill in the art may also construct humanized antibodies from other donor IL-5 antibodies, variable region sequences and CDR peptides described herein. Engineered antibodies can be produced with variable region frameworks potentially recognized as "self" by recipients of the engineered antibody. Minor modifications to the variable region frameworks can be implemented to effect large increases in antigen binding without appreciable increased immunogenicity for the recipient. Such engineered antibodies may effectively treat a human for IL-5 mediated conditions. Such antibodies may also be useful in the diagnosis of such conditions.

VII. Therapeutic/Prophylactic/Diagnostic Uses

This invention also relates to a method of treating humans experiencing eosinophilia-related symptoms, i.e., conditions associated with excess eosinophil production, such as asthma, which comprises administering an effective dose of antibodies including one or more of the engineered antibodies or altered antibodies described herein, or fragments thereof.

The therapeutic response induced by the use of the molecules of this invention is produced by binding to human IL-5 and thus subsequently blocking eosinophil stimulation. Preferably, the molecules of this invention are non-competitive with the IL-5 receptor alpha-chain for binding human IL-5. That is, the preferred molecules of this invention do not block the binding of human IL-5 to the α-chain of the human IL-5 receptor. Thus, the molecules of the present invention, when in preparations and formulations appropriate for therapeutic use, are highly desirable for those persons experiencing an allergic and/or atopic response, or a response associated with eosinophilia, such as but not limited to, allergic rhinitis, asthma, chronic eosinophilic pneumonia, allergic bronchopulmonary aspergillosis, coeliac disease, eosinophilic gastroenteritis, Churg-Strauss syndrome (periarteritis nodosa plus atopy), eosinophilic myalgia syndrome, hypereosinophilic syndrome, oedematous reactions including episodic angiodema, helminth infections, where eosinophils may have a protective role, onchocercal dermatitis and atopic dermatitis.

The altered antibodies, antibodies and fragments thereof of this invention may also be used in conjunction with other antibodies, particularly human mAbs reactive with other markers (epitopes) responsible for the condition against which the engineered antibody of the invention is directed.

The therapeutic agents of this invention are believed to be desirable for treatment of allergic conditions from about 2 days to about 3 weeks, or as needed. For example, longer treatments may be desirable when treating seasonal rhinitis or the like. This represents a considerable advance over the currently used infusion protocol with prior art treatments of IL-5 mediated disorders. The dose and duration of treatment relates to the relative duration of the molecules of the present invention in the human circulation, and can be adjusted by one of skill in the art depending upon the condition being treated and the general health of the patient.

The mode of administration of the therapeutic agent of the invention may be any suitable route which delivers the agent to the host. The altered antibodies, antibodies, engineered antibodies, and fragments thereof, and pharmaceutical compositions of the invention are particularly useful for parenteral administration, i.e., subcutaneously, intramuscularly, intravenously, or intranasally.

Therapeutic agents of the invention may be prepared as pharmaceutical compositions containing an effective amount of the engineered (e.g., humanized) antibody of the invention as an active ingredient in a pharmaceutically acceptable carrier. In the prophylactic agent of the invention, an aqueous suspension or solution containing the engineered antibody, preferably buffered at physiological pH, in a form ready for injection is preferred. The compositions for parenteral administration will commonly comprise a solution of the engineered antibody of the invention or a cocktail thereof dissolved in an pharmaceutically acceptable carrier, preferably an aqueous carrier. A variety of aqueous carriers may be employed, e.g., 0.4% saline, 0.3% glycine, and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antibody of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g. about 50 ng to about 30 mg or more preferably, about 5 mg to about 25 mg, of an engineered antibody of the invention. Similarly, a pharmaceutical composition of the invention for intravenous infusion could be made up to contain about 250 ml of sterile Ringer's solution, and about 1 to about 30 and preferably 5 mg to about 25 mg of an engineered antibody of the invention. Actual methods for preparing parenterally administrable compositions are well known or will be apparent to those skilled in the art and are described in more detail in, for example, Remington's Pharmaceutical Science, 15th ed., Mack Publishing Company, Easton, Pennsylvania.

It is preferred that the therapeutic agent of the invention, when in a pharmaceutical preparation, be present in unit dose forms. The appropriate therapeutically effective dose can be determined readily by those of skill in the art. To effectively treat an inflammatory disorder in a human or other animal, one dose of approximately 0.1 mg to approximately 20 mg per 70 kg body weight of a protein or an antibody of this invention should be administered parenterally, preferably i.v. or i.m. (intramuscularly). Such dose may, if necessary, be repeated at appropriate time intervals selected as appropriate by a physician during the inflammatory response.

The antibodies, altered antibodies and engineered-antibodies of this invention may also be used in diagnostic regimens, such as for the determination of IL-5 mediated disorders or tracking progress of treatment of such disorders. As diagnostic reagents, these antibodies may be conventionally labeled for use in ELISA's and other conventional assay formats for the measurement of IL-5, and/or IL-5/IL-5 receptor α-chain complex levels in serum, plasma or other appropriate tissue, or the release by human cells in culture. The nature of the assay in which the altered antibodies are used are conventional and do not limit this disclosure.

Thus, one embodiment of the present invention relates to a method for aiding the diagnosis of allergies and other conditions associated with excess eosinophil production in a patient which comprises the steps of determining the amount of human IL-5 and/or IL-5/IL-5 receptor α-chain complex in sample (plasma or tissue) obtained from said patient and comparing said determined amount to the mean amount of human IL-5 in the normal population, whereby the presence of a significantly elevated amount of IL-5 and/or IL-5/IL-5 receptor α-chain complex in the patient's sample is an indication of allergies and other conditions associated with excess eosinophil production.

In the compound screening embodiment of this invention, the human IL-5 receptor β-chain is isolated in a membrane fraction, or in cell bound form, and is contacted with a plurality of candidate molecules from which candidates are selected which bind to and interact with the receptor. The candidate compounds can be subjected to a competition screening assays, in which a known ligand, i.e. human IL-5 or IL-5/IL-5 receptor α-chain complex, preferably labeled with an analytically detectable reagent, most preferably radioactivity, is introduced with the drug to be tested and the compound's capacity to inhibit or enhance the binding of the labeled ligand is measured. Alternatively, the binding or interaction can be measured directly by using radioactively labeled candidate compounds of interest or by the second messenger effect resulting from the interaction or binding of the candidate compounds. Compounds are screened for their increased affinity and selectivity to the receptor interest. Molecules that bind gratuitously, i.e., without inducing effects on the human IL-5 receptor β-chain, are most likely to be good antagonists. Potential antagonists include small organic molecules, peptides, polypeptides and antibodies specific for the IL-5 receptor β-chain and thereby inhibit or extinguish its activity.

The antibodies, altered antibodies or fragments thereof described herein can be lyophilized for storage and reconstituted in a suitable carrier prior to use. This technique has been shown to be effective with conventional immunoglobulins and art-known lyophilization and reconstitution techniques can be employed.

The following examples illustrate various aspects of this invention including the construction of exemplary engineered antibodies and expression thereof in suitable vectors and host cells, and are not to be construed as limiting the scope of this invention. All amino acids are identified by conventional three letter or single letter codes. All necessary restriction enzymes, plasmids, and other reagents and materials were obtained from commercial sources unless otherwise indicated. All general cloning ligation and other recombinant DNA methodology were as performed in T. Maniatis et al., cited above, or the second edition thereof (1989), eds. Sambrook et al., by the same publisher ("Sambrook et al.").

EXAMPLE 1

Production of MAbs to hIL-5

Human IL-5 was expressed in Drosophila Schneider 2 (S2) cells and purified to homogeneity. Murine IL-5 was expressed in Baculovirus using Spodoptera frugiperda 21 (Sf21) cells and purified to homogeneity. Monoclonal antibody TRFK-5 (a neutralizing rat anti-mouse IL-5 antibody) was obtained from Genzyme Corp. (Cambridge, Mass.).

A. Immunization Procedure:

Recombinant human IL-5 (IL-5) was used as the immunogen for a panel of seven CAF$_1$ female mice (Charles River, Wilmington, Mass.). The animals received three subcutaneous injections of IL-5 in phosphate buffered saline (PBS) emulsified with a one to one ratio of TiterMAX™ (CytoRx Corp., Norcross, Ga.) over a period of four months. The priming antigen dose was 50 µg (micrograms) and boosts were 25 and 10 µg (micrograms). After the boosts, serum samples were collected and assayed both for binding to IL-5 and for neutralization activity via the receptor binding inhibition assay and B13 proliferation assay (or IL-5 neutralization assay (Example 2C)). All of the mice produced serum samples that bound to IL-5. Animals selected as spleen donors were boosted intravenously with 10 µg (micrograms) of recombinant human IL-5 three days prior to euthanasia.

B. Hybridoma Development:

The fusion procedure, first reported by Kohler et al., (Nature, 256:495 (1975)), was used with modifications to perform the technique using a cell monolayer (Kennet et al., Eds., "Hybridomas: A new dimension in biological analysis", pp. 368–377, Plenum Press, New York). Spleen cells from two donor mice were pooled and fusions performed using a ratio of 50 million spleen cells to ten million SP2/0/Ag14 myeloma cells. Supernatants from fusion-positive wells were assayed for binding to IL-5 by ELISA. Wells containing cells producing antibody to IL-5 were expanded and supernatants screened in an IL-5 receptor binding inhibition assay, and a B 13 (neutralization) proliferation assay (described below).

Sixteen hybridomas were isolated which secreted mAbs reactive with IL-5. The hybridoma supernatants were mixed with iodinated IL-5, added to a membrane extract prepared from Drosophila cells expressing the α-chain of the IL-5 receptor (IL-5R), and assayed for inhibition of receptor binding. Eleven of the hybridoma supernatants inhibited by greater than 60% the binding of iodinated IL-5 to the IL-5 receptor α-chain. Three of the mAbs, 2B6, 2E3 and 2F2, also inhibited by greater than 70% the proliferation of murine B13 cells in response to human but not murine IL-5. Five of the hybridomas, four of which blocked binding and/or proliferation (1C6, 2B6, 2E3 and 2F2) and 1 of which was non-neutralizing (24G9), were repeatedly subcloned in soft agar to generate stable clonal cell lines. Supernatants from the cloned lines were screened for cross-reactivity by ELISA and did not bind to human IL-1α, IL-1β, IL-4, IL-8,M-CSF or TGFα. The mAbs were purified and binding affinities were estimated from optical biosensor (BIAcore) analysis to range from 10 to 100 pM. Supernatants from the lines were isotyped using murine isotyping reagents (PharMingen, San Diego, Calif.). A summary of the affinities and $IC_{50}$ for neutralizing activities of the mAbs is presented in Table I (Example 2).

By similar methods, rat hybridomas were derived from immunized rats, using a comparable immunization protocol and rat myelomas for the fusion as described for the mouse. Two rat hybridomas, 4A6 and 5D3, were identified that produced mAbs which bound to IL-5. Like mAbs 2B6, 2E3 and 2F2, mAbs 4A6 and 5D3 were found to be neutralizing in the B 13 assay described below.

C. Hybridoma Deposit:

The hybridoma cell line SK119-2B6.206.75(1) producing monoclonal antibody 2B6 was deposited with the American Type Culture Collection (ATCC), Rockville, Md., USA, under accession number HB 11783, and has been accepted as a patent deposit, in accordance with the Budapest Treaty of 1977 governing the deposit of microorganisms for the purposes of patent procedure.

The hybridoma cell line SK119-2E3.39.40.2 producing monoclonal antibody 2E3 was deposited with the American Type Culture Collection (ATCC), Rockville, Md., USA, under accession number HB 11782, and has been accepted as a patent deposit, in accordance with the Budapest Treaty of 1977 governing the deposit of microorganisms for the purposes of patent procedure.

The hybridoma cell line SK119-2F2.37.80.12 producing monoclonal antibody 2F2 was deposited with the American Type Culture Collection (ATCC), Rockville, Md., USA, under accession number HB 11781, and has been accepted as a patent deposit, in accordance with the Budapest Treaty of 1977 governing the deposit of microorganisms for the purposes of patent procedure.

The hybridoma cell line SK119-24G9.8.20.5 producing monoclonal antibody 24G9 was deposited with the American Type Culture Collection (ATCC), Rockville, Md., USA, under accession number HB 11780, and has been accepted as a patent deposit, in accordance with the Budapest Treaty of 1977 governing the deposit of microorganisms for the purposes of patent procedure.

The hybridoma cell line 4A6(1)G1F7 producing monoclonal antibody 4A6 was deposited with the American Type Culture Collection (ATCC), Rockville, Md., USA, under accession number HB 11943, and has been accepted as a patent deposit, in accordance with the Budapest Treaty of 1977 governing the deposit of microorganisms for the purposes of patent procedure.

The hybridoma cell line 5D3(1)F5D6 producing monoclonal antibody 5D3 was deposited with the American Type Culture Collection (ATCC), Rockville, Md., USA, under accession number HB 11942, and has been accepted as a patent deposit, in accordance with the Budapest Treaty of 1977 governing the deposit of microorganisms for the purposes of patent procedure.

EXAMPLE 2

Assays

A. ELISA:

Individual wells of MaxiSorb™ immuno plates (Nunc, Naperville, Ill.) were coated with 0.2 ug IL-5 in 0.05M carbonate buffer pH 9.6. After incubating overnight at 4° C., the plates were rinsed with PBS containing 0.025% Tween® 20, and blocked with 1% BSA in PBS with 0.025% Tween® 20 for two hours at room temperature. Undiluted hybrid supernatants were added to the IL-5 coated wells and incubated at room temperature for two hours. After the plates were rinsed, peroxidase labeled goat anti-mouse IgG & IgM (Boehringer Mannheim, Indianapolis, Ind.) was added at 1/7500 dilution in PBS containing 1% BSA and 0.025% Tween® 20. Two hours later the plates were washed and 0.2 ml of 0. 1M citrate buffer pH 4.75 containing 0.1 % urea peroxide and 1 mg/ml orthophenylenediamine was added. After 15 min the plates were read at 450 nm on a VMax™ Microplate Reader (Molecular Devices, Menlo Park, Calif.).

B. Receptor Binding Inhibition Assay:

Membrane extracts of Drosophila S2 cells expressing the α-chain of the human IL-s Receptor (IL-5R) were used to measure the effect of antibody on IL-5 binding to receptor. To prepare the membranes, $10^9$ cells were pelleted at 1000 x g at 4° C. for 10 min. The cell pellet was frozen in a dry ice/ethanol bath for 15 min. The pellet was thawed, resuspended in 10 ml PBS at 4° C. and pelleted at 1000 x g for 10 min. The cell pellet was washed 2X in PBS and resuspended in 13.5 ml Hypotonic buffer (10 mM Tris pH 7.5, 3 mM $MgCl_2$, 1 mM dithiothreitol, 1 mM phenylmethylsulfonyl fluoride, 1 uM leupeptin, 1 uM pepstatin A) and incubated on ice for 5 min. The cell suspension was homogenized in a 15 ml Dounce homogenizer and brought to a final concentration of 0.25M sucrose with a solution of 2.5M sucrose. Cell debris was removed by a 15 min centrifugation at 1000 x g. Cell membranes were pelleted at 100,000 x g at 4° C. for 90 min and resuspended in 50 ml of 10 mM Tris pH 7.5, 3 mM $MgCl_2$, 250 mM sucrose, and stored at −70° C.

Assays with Drosophila membranes containing receptor were performed in MultiscreenGV™ plates (Millipore Corp., Bedford, Mass.) using Drosophila tissue culture medium M3 (Lindquist et al., Drosophila Inf. Serv., 58: 163 (1982)) containing 25 mM HEPES buffer pH 7.2 and 0.1 % BSA (Binding Buffer). Wells were pre-blocked with 0.1 ml binding buffer. 50 ul of the test sample, in triplicate, was added to wells followed by 25 ul iodinated ($^{125}$I) IL-5. After 20 minutes incubation at room temperature, 25 ul of the membrane extract of Drosophila S2 cells expressing the α-chain of the human IL5R was added to the wells. After 1 hour further incubation the membranes were collected by vacuum filtration and washed 3X with binding buffer. Filters were dried and counted.

C. IL-5 Neutralization Assay:

The murine IL-5/IL-3 dependent cell line LyH7.B13 (B 13) was obtained courtesy of R. Palacios, Basel Institute of Immunology, Switzerland. Cells were subcultured twice weekly in RPMI 1640 medium (GibcoBRL, Renfrewshire, UK), supplemented with L-Glutamine, non-essential amino acids, sodium pyruvate, penicillin-streptomycin (all GibcoBRL), plus 2-mercaptoethanol (5 x $10^{-5}$M, Sigma), 10% fetal bovine serum (Globepharm, Surrey, UK) and 1–10 units murine IL-5. For assays, cells were cultured for 48 hours in triplicate (5000 cells/well) in 96-well round bottom plates in the presence of appropriately diluted test samples and pulsed with 0.5 uCi $^3$H-thymidine (Amersham, Bucks, UK) for the final 4 hours. They were processed for scintillation counting in a 1205 Betaplate (LKB Wallac, Beds, UK).

D. Optical Biosensor:

Kinetic and equilibrium binding properties with immobilized hIL-5 and antibodies were measured using a BIAcore optical biosensor (Pharmacia Biosensor, Uppsala, Sweden). Kinetic data were evaluated using relationships described previously (Karlsson et al., *J. Immunol. Meth.*, 145:229–240 (1991)) and which is incorporated by reference in its entirety.

Three of the neutralizing mAbs, namely 2B6, 2E3 and 2F2, had very similar potencies of inhibition of $^{125}$I-IL-5 binding to membrane receptor and neutralization of B cell proliferation and also very similar affinities for IL-5 (see Table I). The nucleotide sequences of the $V_H$ and $V_L$ from these three mAbs, 2 IgG$_1$ and 1 IgG$_{2a}$, respectively, were determined. The sequences obtained were very similar, differing only at a few residues.

TABLE I

Affinity and neutralizing activity of mAbs reactive with human IL-5

| mAb | Kd (pM)$^a$ | Binding IC$_{50}$(nM)$^b$ | Neutralization Proliferation IC$_{50}$$^c$ | 100% Inhibition$^c$ |
|-----|------|------|--------|--------|
| 2B6 | 22 | 1 | 70 | 200 |
| 2E3 | 20 | 1 | 90 | 600 |
| 2F2 | 13 | 1 | 150 | 340 |
| 1C6 | 86 | 43 | 12,200 | ND |
| 24G9 | ND | >133 | >100,000 | ND |
| 4A6 | 18 | >88 | 28 | 100 |
| 5D3 | ND | ND | 100 | 10,000 |

$^a$Determined by optical biosensor (BIAcore) analysis (25° C.)
$^b$Inhibition of $^{125}$I-IL-5 binding to IL-5R(α chain) from Drosophila membranes
$^c$Inhibition of proliferation (in pM) of B13 cells in response to 8 pM human IL-5
ND = No data

EXAMPLE 3

Isolation and Characterization of IL-5 Fabs from Combinatorial Library

A. PCR and Combinatorial Library Construction:

RNA purified from the spleens of three mice was reverse transcribed with a cDNA kit (Boehringer Mannheim, Indianapolis, IN) using either the primer (dT)$_{15}$ supplied with the kit or the 3'Fd (IgG1, IgG2a & IgG3) and kappa light chain primers as described by Huse et al. (*Science*, 246:1275 (1989)) and Kang, S. A. (*Methods: Companion Methods Enzymol.*, 2:111 (1991)) which are hereby incorporated by reference in their entirety. Immunoglobulin cDNAs were amplified by PCR using the primers and the thermal cycling conditions described (Huse et al. supra). The Hot Start technique using AmpliWax™ PCR Gem 100 (Perkin Elmer Cetus, Norwalk, Conn.) beads and the manufacturer's protocol was used for all of the reactions. The PCR products were gel purified, digested, and ligated into the pMKFabGene3 vector (Ames et al., *J. Immunol.*, 152:4572 (1994)). The library titer following ligation with the Fd cDNAs was 5.1×10$^7$ CFU and following ligation with the kappa cDNAs was 1.5×10$^6$ CFU. XL1-Blue cells (Stratagene, La Jolla, Calif.) transformed with the phagemid library were infected with helper phage VCSM13 (Stratagene) and phage were prepared as described by Barbas and Lerner (*Methods: Companion Methods Enzymol.*, 2:119 (1991)).

B. Biopanning:

Four microtiter wells (Immulon II Removawell Strips, Dynatech Laboratories Inc., Chantilly, Va.) were coated overnight at 4° C. with IL-5 (1 ug/well) in 0.1M bicarbonate, pH 8.6. The wells were washed with water and blocked with PBS containing 3% BSA at 37° C. for 1 hour. The blocking solution was removed, and the library was added to microtiter wells (50 ul/well) and incubated at 37° C. for 2 hours. Wells were washed 10 times with TBS/Tween® (50 mM Tris-HCl, pH 7.5, 150 mM NaCl, 0.5% Tween® 20) and once with H$_2$O prior to elution of the adherent phage with 0.1M HCl, adjusted to pH 2.2 with glycine, containing 1 mg/ml BSA.

C. Colony Lifts:

Colony lifts from clones isolated from the third and fourth rounds of biopanning were processed as described (Barbas and Lerner, supra). Filters were incubated for 1 hour at room temperature with 0.5–1.0 uCi $^{125}$I-IL-5, which had been iodinated using Bolton-Hunter reagent (NEN, Billerica, Mass.) following the manufacturers recommended procedure, in PBS containing 1% BSA, washed with PBS 0.25% Tween, and exposed to Kodak XAR film. Colonies expressing IL-5-reactive Fabs were detected by autoradiography.

D. Preparation of Soluble FABs:

Phagemid DNAs were digested with NheI and SpeI to remove gene III and self-ligated. XL1-Blue cells were transformed, and isolated clones were grown overnight at 37° C. in 5.0 ml super broth (SB) medium (30 g tryptone, 20 g yeast extract, 10 g 3-[N-Morpholino]propanesulfonic acid, MOPS with pH adjusted to 7) containing 1% glucose and 50 ug/ml carbenicillin. Cells from 1 ml of this culture were pelleted at 3500 rpm for 10 min in Beckman GS-6R centrifuge and used to inoculate 5 ml SB containing 50 ug/ml carbenicillin. Cultures were shaken for 1 hour at 37° C., Isopopyl-b-D-thiogalactopyranoside (IPTG; 1 mM) was added and the cultures were transferred to 28° C. overnight. Soluble Fab was prepared from periplasmic extracts by lysing the cell pellet for 20 min at 4° C. in 20% sucrose suspended in 30 mM Tris pH 8.0, followed by centrifugation in a Microfuge for 10 min. Fab concentrations were estimated by western blot by comparison to samples containing known amounts of murine Fab. The different bacterial periplasmic extracts contained similar concentrations of Fab, ranging from 1 to 20 ug/ml, as estimated by western blot analysis.

E. Purification of FABs:

A chelating peptide was engineered onto the carboxy-terminal end of the heavy chain to aid in protein purification. Following removal of the M13 geneIII coding region, via digestion with NheI and SpeI, a pair of overlapping oligonucleotides:

[SEQ ID NO: 43] 5'-CTAGCCACCACCACCACCACCACTAA-3';

[SEQ ID NO: 44] 3'-GGTGGTGGTGGTGGTGGTGATTGATC-5' encoding six histidine residues were subcloned into the Fab expression vector. Induction of Fab expression was performed as described above. Following overnight induction at 28° C. periplasmic lysate of the cell pellet was prepared by 30 min incubation at 4° C. in 20% sucrose, 30 mM TRIS pH 8.0. Urea and Brij-35 detergent were added to the clarified supernatant to final concentrations of 2M and 1% respectively. After stirring at room temperature for 1 hour, the treated and clarified supernatant was loaded at 0.5 ml/min directly onto a 5 ml Nickel-NTA metal chelating column (1.5×3 cm) equilibrated with buffer A (100 mM Na-Phosphate, 10 mM Tris, 0.3M NaCl, 2M urea, pH 8.0). After a 4 column volume (20 ml) wash bound materials were eluted with a 6 column volume (30 ml) reverse pH gradient from pH 8 to pH 4 in the same buffer as above. The purified Fabs eluted from the column in a sharp symmetrical peak at pH 5.5. They were >90% pure and free of DNA.

F. FAB ELISA:

Immulon II plates (Dynatech) were coated overnight at 4° C. with protein suspended (1 mg/ml; 50 ml per well) in 0.1M bicarbonate buffer, pH 8.6. Dilutions and washes were performed in PBS containing 0.05% Tween™ 20. Plates were washed and blocked for 1 hour with PBS containing 1% BSA at room temperature. Various dilutions of the bacterial supernatants containing soluble Fabs, or purified Fabs, were added to the plates. Following a one hour incubation plates were washed and biotinylated goat anti-mouse kappa (Southern Biotechnology Associates, Inc., Birmingham, AL) was added (1:2000 dilution; 50 ul/well) for 1 hour. The plates were washed and streptavidin labeled horseradish peroxidase was added (1:2000 dilution; 50 ul/well) for 1 hour. The plates were washed, ABTS peroxidase substrate was added (100 ul/well; Kirkegaard & Perry Laboratories, Gaithersburg, Md.) and the optical density at 405 nm was read on a UVmax™ (Molecular Devices) microplate reader.

G. Isolation and Characterization of Fabs from a Combinatorial Library:

Phage bearing Fabs to IL-5 were selected from the library by multiple rounds of biopanning against microtiter wells coated with IL-5. After 4 rounds of selection IL-5 reactive Fabs were identified by a colony lift assay using $^{125}$I-IL-5. Thirty four colonies from the third round and 4 colonies from the fourth round were identified which bound labeled IL-5. Binding to IL-5 was confirmed by direct binding ELISA using culture supernatants expressing the Fab-geneIII fusion protein. DNA was isolated from these colonies and, after removing the coding region of M13 gene III, soluble Fab expression was induced. Periplasmic fractions were prepared and assayed by ELISA for binding to IL-5. The Fabs bound specifically to IL-5 with no demonstrable binding to an another protein, rC5a.

The undiluted periplasmic extracts (containing 1 to 20 ug/mil Fab) were assayed in the IL-5R binding inhibition assay (Example 2). None of the Fabs inhibited binding of iodinated IL-5 to the IL-5Rα by more than 35%.

H. Conversion of Neutralizing mAb to a FAB:

The Fd and k cDNAs of mAb (2B6) were isolated by PCR using the conditions described above. The gel-purified fragments were subcloned into the pMKFabGene3 vector which had been modified to include the hexa-His sequence 3' of the gene III cDNA, resulting in the plasmid pMKFabGene3H. A functional, IL-5 binding Fab clone containing the 2B6 heavy and light chains was identified by a colony lift assay. Upon removal gene III via Nhe I/SpeI I digestion and self-ligation the heavy chain was fused in frame to the hexa-His, allowing purification as described above. In a dose dependent manner, this Fab inhibited receptor binding with an IC50 of approximately 7.5 ug/ml, similar to that of the parent mAb, murine 2B6.

I. Construction and Screening of Chain-Shuffled Library:

The cDNA encoding the Fd of the neutralizing mAb 2B6 was subcloned as an XhoI/SpeI fragment into pMKFabGene3H which contained a SstI/XbaI fragment in lieu of a light chain cDNA. This phagemid was digested with SstI and XbaI and ligated with the SstI/XbaI digested light chain PCR product derived from the IL-5 immunized mice (described above). The library titer following ligation was 4×10$^5$ CFU. Biopanning, and colony lift assay was performed as described above for the combinatorial library.

The library was constructed by pairing the cDNA encoding the Fd of the neutralizing mAb 2B6 with the same light chain repertoire, recovered from the IL-5 immunized mice, used to generate the combinatorial library. This chain shuffled library was subjected to 4 rounds of biopanning vs immobilized IL-5 and the resultant colonies were assayed for IL-5 reactivity using the colony lift assay. Positive colonies, which bound iodinated IL-5, were further assayed by ELISA and the IL-5Rα binding assay. Two of the Fabs, 2 & 15, recovered from the chain shuffled library blocked binding of IL-5 to the IL-5Rα and inhibited IL-5 dependent proliferation in the B13 assay. The sequences of these 2 Vks were similar to the sequence of the 2B6 Vk, the original light chain partner for the 2B6 $V_H$. The light chain sequences for Fab 2 & 15 are SEQ ID NOs: 45 and 46, respectively. For Fab 2, CDRs 1–3 are SEQ ID NOs: 10, 11 and 47, respectively. For Fab 15, CDRs 1–3 are SEQ ID NOs: 10, 11 and 48, respectively.

All antibody amino acid sequences listed below in Examples 4 and 5 use the KABAT numbering system which allows variability in CDR and framework lengths. That is, key amino acids are always assigned the same number regardless of the actual number of amino acids preceding them. For example, the cysteine preceding CDR1 of all light chains is always KABAT position 23 and the tryptophan residue following CDR1 is always KABAT position 35 even though CDR1 may contain up to 17 amino acids.

EXAMPLE 4

Humanized Antibody

One humanized antibody was designed to contain murine CDRs within a human antibody framework. This humanized version of the IL-5 specific mouse antibody 2B6, was prepared by performing the following manipulations.

A. Gene Cloning:

mRNA was isolated from each of the respective 2B6, 2F2 and 2E3 hybridoma cell lines (see Example 1) with a kit obtained from Boehringer Mannheim (Indianapolis, IN) and then reverse transcribed using the primer (dT)$_{15}$ supplied with a cDNA kit (Boehringer Mannheim) to make cDNA. PCR primers specific for mouse immunoglobulin were used to amplify DNA coding for domains extending from amino acid #9 (KABAT numbering system) of the heavy chain variable region to the hinge region and from amino acid #9 (KABAT numbering system) of the light chain variable region to the end of the constant region. Several clones of each antibody chain were obtained by independent PCR reactions.

The mouse gamma 1 hinge region primer used is [SEQ ID NO: 22]:

5' GTACATATGCAAGGCTTACAACCACAATC 3'.

The mouse gamma 2a hinge region primer used is [SEQ ID NO: 23]:

5' GGACAGGGCTTACTAGTGGGCCCTCTGGGCTC 3'

The mouse heavy chain variable region primer used is [SEQ ID NO: 24]:

5'AGGT(C or G)(C or A)A(G or A)CT(G or T)TCTCGAGTC(T or A)GG 3'

The mouse kappa chain constant region primer used is [SEQ ID NO: 25]:

5' CTAACACTCATTCCTGTTGAAGCTCTTGACAATGGG 3'

The mouse light chain variable region primer is [SEQ ID NO: 26]:

5' CCAGATGTGAGCTCGTGATGACCCAGACTCCA 3'

The PCR fragments were cloned into plasmids pGEM7f+ (Promega) that were then transformed into *E. coli* DH5a (Bethesda Research Labs).

B. DNA Sequencing:

The heavy and light chain murine cDNA clones from Part A above were sequenced. The results of sequencing of the variable regions of these clones are shown in SEQ ID NOs: 1–6 (FIG. 1-6). Each clone contained amino acids known to be conserved among mouse heavy chain variable regions or light chain variable regions. The CDR amino acid sequences are listed below.

The CDR regions for the 2B6 heavy chain are SEQ ID NOs: 7, 8 and 9. See FIG. 7. These sequences are encoded by SEQ ID NO: 1. The CDR regions for the light chain are SEQ ID NOs: 10, 11 and 12. See FIG. 7. These sequences are encoded by SEQ ID NO:2.

The CDR regions for the 2F2 heavy chain are SEQ ID NOs: 7, 8 and 9. See FIG. 7. These sequences are encoded by SEQ ID NO:3. The CDR regions for the light chain are SEQ ID NOs: 10, 11 and 13. See FIG. 7. These sequences are encoded by SEQ ID NO:4.

The CDR regions for the 2E3 heavy chain are SEQ ID NOs: 7, 8 and 14. See FIG. 7. These sequences are encoded by SEQ ID NO:5. The CDR regions for the light chain are SEQ ID NOs: 10, 11 and 13. See FIG. 7. These sequences are encoded by SEQ ID NO:6.

C. Selection of Human Frameworks:

Following the cloning of 2B6, the amino acid sequences of the variable region heavy and light chains (FIGS. 1 and 2) (SEQ ID NOs: 15 and 16, respectively) were compared with the known murine immunoglobulin sequences in the KABAT and SWISS-PROT (*Nuc. Acids Res.*, 20:2019–2022 (1992)) protein sequence databases in order to assign amino acids to the N-terminal residues. The 2B6 heavy and light chain variable region deduced amino acid sequences were then compared with the human immunoglobulin protein sequence databases in order to identify a human framework for both the heavy and light chains which would most closely match the murine sequence. In addition, the heavy and light chains were evaluated with a positional database generated from structural models of the Fab domain to assess potential conflicts due to amino acids which might influence CDR presentation. Conflicts were resolved during synthesis of the humanized variable region frameworks by substitution of the corresponding mouse amino acid at that location.

The heavy chain framework regions of an antibody obtained from a human myeloma immunoglobulin (COR) was used (E. M. Press and N. M. Hogg, *Biochem. J.*, 117:641–660 (1970)). The human heavy chain framework amino acid sequence was found to be approximately 66% homologous to the 2B6 framework.

For a suitable light chain variable region framework, the light chain variable framework sequence of the Bence-Jones protein, (LEN) (Schneider et al., *Hoppe-Seyler's Z. Physiol. Chem.*, 356:507–557 (1975)), was used. The human light chain framework regions were approximately 82% homologous to the murine 2B6 light chain framework regions, at the amino acid level.

The selected human frameworks were back translated to provide a DNA sequence.

D. Construction of Humanized MAb Genes:

Given the 2B6 heavy chain CDRs [FIG. 7 and SEQ ID NOs: 1–2] and the framework sequences of the human antibodies, a synthetic heavy chain variable region was made [SEQ ID NO: 18]. This was made using four synthetic oligonucleotides [SEQ ID NOs:27 and 28] [ SEQ ID NOs: 29 and 30] which, when joined, coded for amino acids #21–#106 (KABAT numeration). The oligonucleotides were then ligated into the HpaI-KpnI restriction sites of a pUC18 based plasmid containing sequences derived from another humanized heavy chain based on the COR framework (supra). This plasmid provides a signal sequence [SEQ ID NO: 17] and the remaining variable region sequence. Any errors in the mapped sequence were corrected by PCR with mutagenic primers or by the addition of synthetic linkers into existing restriction sites.

Figure 10:
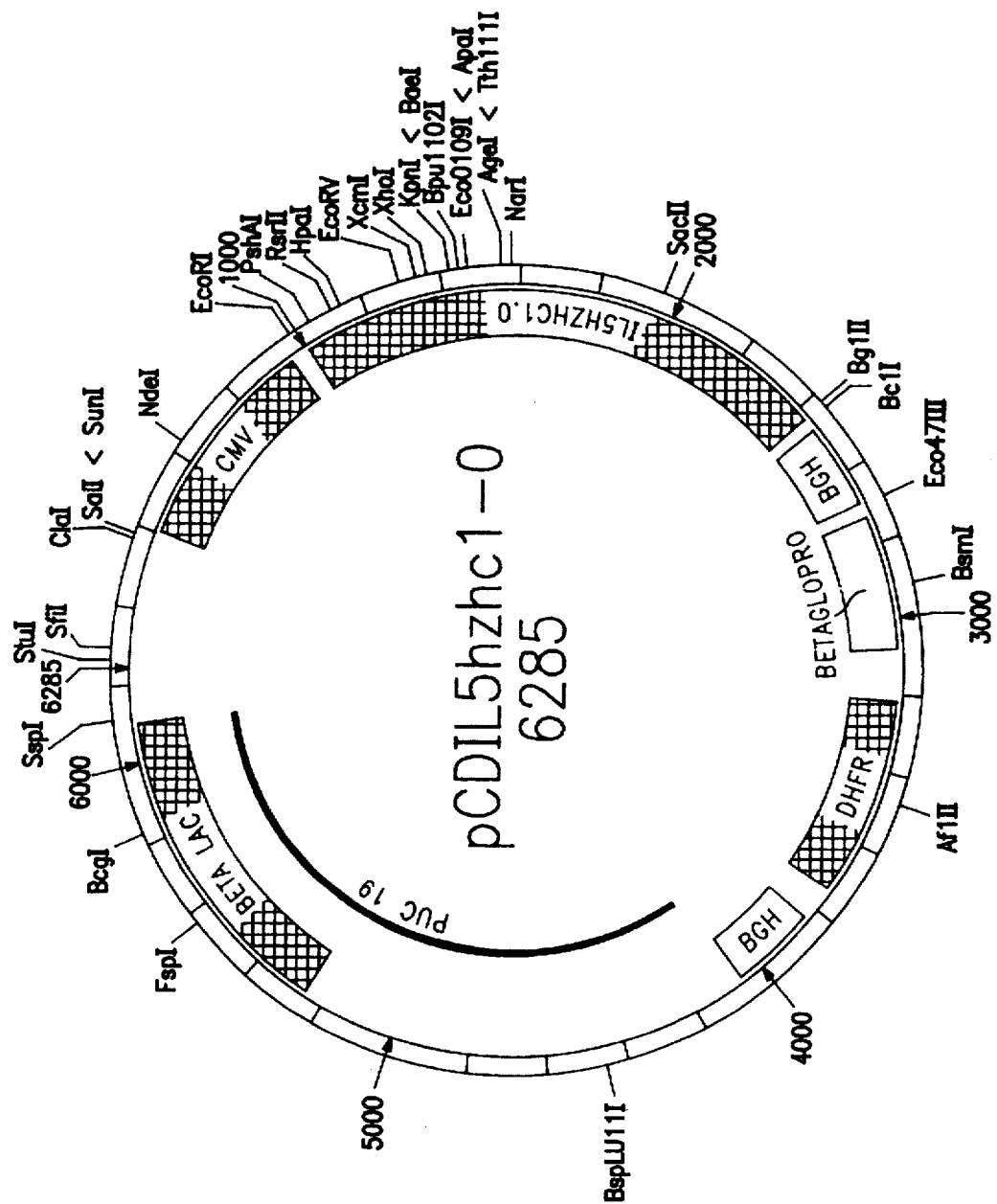

The signal sequence and humanized heavy chain variable region were excised from the pUC based plasmid as a EcoRI-ApaI fragment and ligated into the expression vector pCD that contained an $IgG_1$ human constant region. The synthetic heavy chain variable region nucleotide and amino acid sequences are provided in FIG. 8 [SEQ ID NOs: 18 and 19]. The human framework residues are amino acids 1–30, 36–49, 66–97 and 109–119 of SEQ ID NO: 19. The amino acid sequences of the CDRs are identical to the murine 2B6 CDRs. The resulting expression vector, pCDIL5HZHC1.0, is shown in FIG. 10.

Given the 2B6 light chain CDRs [FIG. 7 and SEQ ID NOs: 10, 11 and 12] and the framework sequence of the human antibody, a synthetic light chain variable region was made [SEQ ID NO: 20]. Four synthetic oligonucleotides coding for amino acids #27–#58 (KABAT numeration)[SEQ ID NOs:31 and 32] and amino acids #80–#109 [SEQ ID NOs:33 and 34] of the humanized $V_L$ with SacI-KpnI and PstI-HindIII ends respectively, were inserted into a pUC18 based plasmid containing sequences derived from another human light chain framework (B 17) (Marsh et al, *Nuc. Acids Res.*, 13:6531–6544 (1985)) which shares a high degree of homology to the LEN framework. This plasmid provides the remaining variable region sequence. Any errors in the mapped sequence and the single amino acid difference between the LEN and B 17 frameworks were corrected by PCR with mutagenic primers or by the addition of synthetic linkers into existing restriction sites.

The humanized light chain variable region was isolated from the pUC plasmid as a EcoRV-NarI fragment and ligated into the expression vector pCN that contained a signal sequence [SEQ ID NO: 17] along with a kappa human constant region. The synthetic light chain variable region nucleotide and amino acid sequences are provided in FIG. 9 [SEQ ID NOs:20 and 21]. The human framework residues are amino acids 1–23, 41–55, 63–94 and 104–113 of SEQ ID NO: 21. The amino acid sequences of the CDRs are identical to the murine 2B6 CDRs. However, the coding sequences for these CDRs differ from the murine 2B6 coding sequences to allow creation of restriction enzyme sites. One of the resulting expression vectors, pCNIL5HZLC1.0, is shown in FIG. 11. These synthetic variable light and/or heavy chain sequences are employed in the construction of a humanized antibody.

E. Expression of Humanized MAb:

The humanized heavy chain, derived from an $IgG_1$ isotype, utilizes a synthetic heavy chain variable region as provided in SEQ ID NO: 19. This synthetic $V_H$ containing the 2B6 heavy chain CDRs was designed and synthesized as described above.

The humanized light chain, a human kappa chain, utilizes a synthetic light chain variable region as provided in SEQ ID NO: 21. This synthetic V_L containing the 2B6 light chain CDRs was designed and synthesized as described above. The DNA fragments coding for the humanized variable regions were inserted into pUC19-based mammalian cell expression plasmids that utilize a signal sequence and contain CMV promoters and the human heavy chain or human light chain constant regions of the chimera produced in Example 5 below, by conventional methods (Maniatis et al., cited above) to yield the plasmids pCDIL5HZHC1.0 (heavy chain) [SEQ ID NO: 49, see also FIG. 10] and pCNIL5HZLC1.0 (light chain) [SEQ ID NO: 50, see also FIG. 11]. The plasmids were co-transfected into COS cells and supernatants assayed after three and five days, respectively, by the ELISA described in Example 5 for the presence of human antibody.

The above example describes the preparation of an exemplary engineered antibody. Similar procedures may be followed for the development of other engineered antibodies, using other anti-IL-5 antibodies (e.g., 2F2, 2E3, 4A6, 5D3, 24G9, etc.) developed by conventional means.

F. Purification:

Purification of CHO expressed chimeric and humanized 2B6 can be achieved by conventional protein A (or G) affinity chromatography followed by ion exchange and molecular sieve chromatography. Similar processes have been successfully employed for the purification to >95% purity of other mAbs (e.g., to respiratory syncytial virus, interleukin-4 and malaria circumsporozoite antigens).

G. Additional Humanized mAbs and Expression Plasmids:

Given the plasmid pCDIL5HZHC1.0 [SEQ ID NO: 49] the expression plasmid pCDIL5HZHC1.1 was made that substitutes an Asparagine for Threonine at framework position 73. This was done by ligating a synthetic linker with EcoRV and XhoI ends [SEQ ID NO: 51 and SEQ ID NO: 52] into identically digested pCDIL5HZHC1.0. Similarly, the expression plasmid pCDIL5HZHC1.2 substitutes an Isoleucine for Valine at framework position 37. This was accomplished by ligating a synthetic linker with HpaI and XbaI ends [SEQ ID NO: 53 and SEQ ID NO: 54] into identically digested pCDIL5HZHC1.0. The expression plasmid pCDIL5HZHC1.3 was also made by ligating a synthetic linker with HpaI and XbaI ends [SEQ ID NO: 53 and SEQ ID NO: 54] into identically digested pCDIL5HZHC 1.1.

Given the pUC18 based plasmid described previously which contains DNA sequences of four synthetic oligonucleotides [SEQ ID NOs: 31, 32, 33 and 34], a humanized light chain variable region was made where framework position #15 is changed from a Leucine to Alanine. This plasmid was digested with NheI and SacI restriction endonucleases and a synthetic linker [SEQ ID NOs: 55 and 56] was inserted. An EcoRV-NarI fragment was then isolated and ligated into the identically digested expression vector pCNIL5HZLC 1.0 to create pCNIL5HZLC . 1.

A synthetic variable region was made using the heavy chain framework regions obtained from immunoglobulin (NEW) (Saul et al. *J. Biol. Chem.* 253:585–597(1978)) and the 2B6 heavy chain CDRs [FIG. 7 and SEQ ID NOs: 1–2]. Framework amino acids which might influence CDR presentation were identified and substitutions made using methods described previously. Four overlapping synthetic oligonucleotides were generated [SEQ ID NOs: 57, 58, 59 and 60] which, when annealed and extended, code for amino acids representing a signal sequence [SEQ ID NO: 17] and a heavy chain variable region. This synthetic gene was then amplified using PCR primers [SEQ ID NOs: 63 and 64] and ligated as a BstXI-HindIII restriction fragment into a pUC18 based plasmid containing sequences derived from another humanized heavy chain based on the COR framework. A phenylalanine to tyrosine framework substitution was made at amino acid position 91 (Kabat numbering system) (equivalent to position 94 of FIG. 12) by inserting a synthetic oligonucleotide linker [SEQ ID NOs: 75 and 76] into SacII and KpnI restriction sites. The resulting heavy chain variable region [FIG. 12 and SEQ ID NOs: 61, 62] is referred to as the NEWM humanized heavy chain.

Any errors in the mapped sequence were corrected by PCR with mutagenic primers or by the addition of synthetic linkers into existing restriction sites. The signal sequence and humanized heavy chain variable region were excised from the pUC based plasmid as a EcoRi-ApaI fragment and ligated into the expression vector pCD that contained a human IgGi constant region to create the plasmid pCDL5NEWM. The amino acid sequences of the CDRs are identical to the murine 2B6 heavy chain CDRs.

A synthetic variable region was made using the light chain framework regions obtained from immunoglobulin (REI) (Palm et al. *Hoppe-Seyler's Z. Physiol. Chem.* 356:167–191 (1975)) and the 2B6 light chain CDRs [FIG. 7 and SEQ ID NOs: 10, 11 and 12]. Framework amino acids which might influence CDR presentation were identified and substitutions made using methods described previously. Four overlapping synthetic oligonucleotides were generated [SEQ ID NOs: 65, 66, 67 and 68] which, when annealed and extended, code for amino acids representing a light chain variable region [FIG. 13 and SEQ ID NOs: 69, 70] referred to as the REI humanized light chain. This synthetic gene was then amplified using PCR primers [SEQ ID NOs: 71 and 72] and ligated as an EcoRi-HindIII restriction fragment into pGEM-7Zf(+) (Promega Corporation, Madison, Wis.).

Any errors in the mapped sequence were corrected by PCR with mutagenic primers or by the addition of synthetic linkers into existing restriction sites. The humanized light chain variable region was excised from the pGEM-7Zf(+) based plasmid as an EcoRV-NarI fragment and ligated into the expression vector pCN that contained a signal sequence [SEQ ID NO: 17] along with a human Kappa constant region to create the plasmid pCNIL5REI. The amino acid sequences of the CDRs are identical to the murine 2B6 light chain CDRs. However, the coding sequences for these CDRs differ from the murine 2B6 coding sequences to allow creation of restriction enzyme sites. These synthetic variable light and/or heavy chain sequences are employed in the construction of a humanized antibody.

Given the pGEM-7Zf(+) based plasmid described above, a humanized light chain variable region can be made where framework position #15 is changed from a Valine to Alanine. This plasmid may be digested with NheI and SacI restriction endonucleases and a synthetic linker [SEQ ID NOs: 73 and 74] is inserted. An EcoRV-NarI fragment may then be isolated and ligated into the identically digested expression vector pCNIL5HZREI to create the plasmid pCNIL5REI_{V15A}.

EXAMPLE 5

Construction of a Chimeric Antibody

DNA coding for amino acids #9-#104 (KABAT numeration) of the murine mAb 2B6 heavy chain variable region was isolated as a AvaII-StyI restriction fragment from a pGEM7Zf+ based PCR clone of cDNA generated from the 2B6 hybridoma cell line (see Example 4). The flanking heavy chain variable region sequences and a signal sequence [SEQ ID NO: 17] were provided by combining this fragment along with four small synthetic oligomer linkers [SEQ ID NOs: 35 and 36] [SEQ ID NOs: 37 and 38] into a pUC18 based plasmid digested with BstX1-HindIII. A consensus of N-terminal amino acids deduced from closely related murine heavy chains were assigned for the first eight $V_H$ residues and are coded within SEQ ID NOs: 35 and 36. The deduced amino acid sequence of the heavy chain was verified by the sequencing of the first 15 N-terminal amino acids of the 2B6 heavy chain.

An EcoRI-ApaI fragment containing sequence for signal and $V_H$ regions was isolated and ligated into plasmid pCD that already encodes the human IgGi constant region.

DNA coding for amino acids #12–#99 (KABAT nomenclature) of the murine mAb 2B6 light chain variable region was isolated as a DdeI-AvaI restriction fragment from a pGEM7Zf+ based PCR clone of cDNA generated from the 2B6 hybridoma cell line (see Example 4). The flanking light chain variable region sequences were provided by combining this fragment along with four small synthetic oligomer linkers [SEQ ID NOs: 39 and 40] [SEQ ID NOs: 41 and 42] into a pUC18 based plasmid digested with EcoRV-HindIII. A consensus of N-terminal amino acids deduced from closely related murine light chains were assigned for the first eight $V_L$ residues and are coded within SEQ ID NOs: 39 and 40. The deduced amino acid sequence of the light chain was verified by the sequencing of the first 15 N-terminal amino acids of the 2B6 light chain. This variable region was then isolated as a EcoRV-NarI fragment and ligated into the expression vector pCN that already contains the human kappa region and a signal sequence.

Expression of a chimeric antibody was accomplished by co-transfection of the pCD and pCN based plasmids into COS cells. Culture supernatants were collected three and five days later and assayed for immunoglobulin expression by ELISA described as follows: Each step except for the last is followed by PBS washes. Microtiter plates were coated overnight with 100 ng/50 ul/well of a goat antibody specific for the Fc region of human antibodies. The culture supernatants were added and incubated for 1 hour. Horseradish peroxidase conjugated goat anti-human IgG antibody was then added and allowed to incubate for 1 hour. This was followed by addition of ABTS peroxidase substrate (Kirkegaard & Perry Laboratories Inc., Gaithersburg, Md.). After 1 hour incubation, the absorbance at 405 nm was read on a microtiter plate reader (Molecular Devices Corporation, Menlo Park, Calif.). Expression of the chimeric antibody was detected. In a similar ELISA, the COS cell supernatants, containing the chimeric antibody, bound specifically to microtiter wells coated with human IL-5 protein. This result confirmed that genes coding for an antibody to IL-5 had been synthesized and expressed.

The above example describes the preparation of an exemplary engineered antibody. Similar procedures may be followed for the development of other engineered antibodies, using other anti-IL-5 donor antibodies (e.g., 2F2, 2E3, 4A6, 5D3, 24G9, etc.) developed by conventional means.

EXAMPLE 6

Human IL-5/hIL-5 Receptor α-chain/MAb Complex

A. ELISA

The following antibodies were evaluated: 24G9 (non-neutralizing), 4A6 (neutralizing) and 2B6 (neutralizing), at concentrations between 2ng/ml–32ng/ml.

Flat bottomed ELISA plate wells (Wallac) were coated overnight with 100 ul Protein-A (5 ug/ml) at 4° C. Following aspiration, wells were blocked with 200ul blocking buffer containing 1% BSA and incubated for 60 min at 37° C. Plates were washed 4x and 100 ul soluble IL-5Ralpha-Fc (see Johnson et al., (1995) *J Biol Chem*, 270: 9459–9471) (2.25 ug/ml) added to each well and incubated at 37° C. for 30 min. Plates were washed 1x and increasing concentrations of recombinant human IL-5 added to each well. Following a 30 min incubation at 37° C., wells were washed once and 100 ul antibody (2 ug/ml) added and incubated for 60 min at 37° C. Plates were washed 4x and 100 ul biotin-labelled goat anti-mouse Ig or goat anti-rat Ig (Sigma) added to each well. Plates were incubated for 60 min at 37° C. and washed 4x. Europium-labelled streptavidin (Wallac) was diluted to 1:1000 in europium buffer (Wallac) and 100 ul volumes added to each well. Plates were incubated for 30 min at 37° C. and washed 6x. Enhancer solution (Wallac) was added to each well and plates read using a 1234 Delphia research fluorometer.

There was a dose-dependent increase in binding of mAbs 24G9 and 4A6 to the IL-5/IL-5 receptor complex. No such increase was seen using mAb 2B6.MAb 2B6 inhibits binding of IL-5 to the IL-5Ralpha chain. In contrast neither 24G9 or 4A6 inhibited binding of IL-5 to the IL-5Ralpha chain. See Table II.

TABLE II

| Binding to hIL-5/IL-5 Receptor α-chain Complex (Counts) | | | |
|---|---|---|---|
| Concentration (ng/ml/mAb) | 24G9 | 2B6 | 4A6 |
| 0 | 4975 | 2767 | 6733 |
| 2 | 6338 | 2939 | 8227 |
| 8 | 10521 | 3196 | 13957 |
| 32 | 33911 | 4977 | 33143 |

B. Optical Biosensor (1) MAb 4A6 was immobilized onto a BIAcore chip (see Example 2D). hIL-5 (25ul) was passed onto the 4A6 surface at a flow rate of 5 ul/min. IL-5 receptor α-chain (@ 15, 30, 60, 120 nM, in 25 ul) was then injected. The kinetics of IL-5 receptor α-chain (Ra) in binding to 4A6/IL-5 complex can be calculated as: Kon=6.3×10$^5$(/M/s); Koff=2.3×10$^{-3}$ (/s). The kinetics for IL-5-IL-5Pα interaction is: Kon=7.5×10$^5$(/M/s); Koff=2.8×10$^{-3}$ (/s). Thus, mAb 4A6 has no significant effect on the interaction between IL-5 and IL-5 receptor α-chain.

(2) hIL-5 was immobilized on a BIAcore chip. MAb 4A6 (25 ul, 32 ug/ml) was injected onto the surface, followed by injection of IL-5 receptor α-chain (20 ul, 90 nM). As a control, the same amount of IL-5 receptor α-chain was injected directly onto the IL-5 surface. Pre-binding of mAb 4A6 to hIL5 did not block binding of IL-5 receptor α-chain to hIL-5.

(3) Protein A was immobilized on a BIAcore chip. IL-5Ra-Fc (30 ul, 20 ug/ml) was injected onto the protein A surface. IL-5 (25 ul, 80 nM) was then captured by IL-5Rα-Fc, followed by binding of mAb 24G9 (25 ul, 32 ug/ml). MAb 24G9 bound to the hIL-5/IL-5Rα complex.

(4) MAb 24G9 was immobilized on a BIAcore chip. IL-5 was captured to the 24G9 surface, followed by injections of different mAbs. Mabs 2B6, TRFK5 and CMX5-2 bind to the IL-5/24G9 complex, while binding of mAb 4A6 to IL-5 was blocked. This indicates that 4A6 and 24G9 share binding epitopes.

C. Sedimentation Velocity

A three component mixture of hIL-5, mAb 4A6, and a soluble IL-5 receptor α-chain was analyzed by sedimentation velocity after 14 hours (20° C.). A complex corresponding to the same size as a soluble IL-5 receptor α-chain/hIL-5/mAb complex was observed.

What is claimed is:

1. An improved method for treating interleukin-5(IL-5) mediated conditions associated with excess eosinophil productions wherein the improvement comprises the step of:

administering a neutralizing monoclonal antibody for human IL-5 which does not block binding of human IL-5 to the α-chain of the human IL-5 receptor and which binds both free and receptor complexed IL-5 in an amount effective to ameliorate the symptoms of said conditions.

2. The method according to claim 1 wherein the monoclonal antibody has all of the identifying characteristics of mAb 4A6.

3. The method according to claim 1 wherein the monoclonal antibody is—a CDR-grafted—antibody comprising a heavy chain and a light chain, wherein the framework regions of said heavy and light chains are —obtained—from at least one —human—antibody and the amino acid sequences of the complementarity determining regions of each said —chains—are—obtained—from the monoclonal antibody 4A6—produced by HB 11943—.

4. The method of claim 1 wherein said condition associated with excess eosinophil production is asthma.

5. The method of claim 1 wherein said condition associated with excess eosinophil production is allergic rhinitis.

6. The method of claim 1 wherein said condition associated with excess eosinophil production is atopic dermatitis.

7. A method to assess the presence or absence of a human IL-5 soluble receptor α-chain/human IL-5 complex in a human which comprises:

obtaining a sample of biological fluid from a patient and allowing a monoclonal antibody for human IL-5 which does not block binding of human IL-5 to the α-chain of the human IL-5 receptor to come in contact with such sample under conditions such that a human IL-5 soluble receptor α-chain/human IL-5/monoclonal antibody complex can form; and detecting the presence or absence of said human IL-5 soluble receptor α-chain/human IL-5/ monoclonal antibody complex.

8. A method for aiding in the diagnosis of allergies and other IL-5 mediated conditions associated with excess eosinophil production comprising the steps of:

determining the amount of human IL-5 soluble receptor α-chain/human IL-5 complex in a sample of a patient according to the method of claim 7; and comparing said determined amount to a reference range of human IL-5 soluble receptor α-chain/human IL-5 complex, whereby the presence of a determined amount of human IL-5 soluble receptor α-chain in/human IL-5 complex in the patient outside said reference range is an indication of allergies and other IL-5 mediated conditions associated with excess eosinophil production.

9. A method of screening compounds to identify those compounds which antagonize binding of a human IL-5 soluble receptor α-chain/human IL-5 complex to a human IL-5 receptor β-chain which method comprises:

contacting the human IL-5 receptor α-chain with at least one candidate compound under conditions to permit binding to the receptor, and identifying those candidate compounds that antagonize binding of a human IL-5 soluble receptor α-chain/human IL-5 complex.

10. A method of screening compounds to identify those compounds which antagonize binding of a human IL-5 soluble receptor α-chain / human IL-5/monoclonal antibody for human IL-5 which does not block binding of human IL-5 to the α-chain of the human IL-5 receptor complex to a human IL-5 receptor β-chain, which method comprises:

contacting the human IL-5 receptor β-chain with at least one candidate compound under conditions to permit binding to the IL-5 receptor β-chain; and identifying those candidate compounds that antagonize binding of said receptor/IL-5/antibody complex to the IL-5 receptor β-chain.

* * * * *